(12) United States Patent
Yu et al.

(10) Patent No.: US 9,073,944 B2
(45) Date of Patent: Jul. 7, 2015

(54) CYCLIC DIAMINOPYRIMIDINE DERIVATIVES

(71) Applicant: Merck Patent GmbH, Darmstadt (DE)

(72) Inventors: Henry Yu, Wellesley, MA (US); Lizbeth Celeste Deselm, Melrose, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/379,625

(22) PCT Filed: Dec. 18, 2012

(86) PCT No.: PCT/US2012/070252
§ 371 (c)(1),
(2) Date: Aug. 19, 2014

(87) PCT Pub. No.: WO2013/126132
PCT Pub. Date: Aug. 29, 2013

(65) Prior Publication Data
US 2015/0025066 A1    Jan. 22, 2015

Related U.S. Application Data

(60) Provisional application No. 61/601,101, filed on Feb. 21, 2012.

(51) Int. Cl.
| | | |
|---|---|---|
| *C07D 413/12* | (2006.01) | |
| *C07D 413/14* | (2006.01) | |
| *C07D 498/14* | (2006.01) | |
| *A61K 31/5383* | (2006.01) | |
| *C07D 498/22* | (2006.01) | |

(52) U.S. Cl.
CPC ............. *C07D 498/14* (2013.01); *C07D 413/14* (2013.01); *C07D 413/12* (2013.01); *A61K 31/5383* (2013.01); *C07D 498/22* (2013.01)

(58) Field of Classification Search
CPC ........................... C07D 413/12; C07D 413/14
See application file for complete search history.

(56) References Cited

FOREIGN PATENT DOCUMENTS

| WO | 97/22596 A1 | 6/1997 |
|---|---|---|
| WO | 97/30035 A1 | 8/1997 |
| WO | 97/32856 A1 | 9/1997 |
| WO | 98/13354 A1 | 4/1998 |
| WO | 99/02166 A1 | 1/1999 |
| WO | 00/40529 A1 | 7/2000 |
| WO | 00/41669 A2 | 7/2000 |
| WO | 01/92224 A1 | 12/2001 |
| WO | 02/04434 A1 | 1/2002 |
| WO | 02/08213 A1 | 1/2002 |
| WO | 2007/111720 A2 | 10/2007 |
| WO | 2010/028116 A1 | 3/2010 |

OTHER PUBLICATIONS

Foster, Advances in Drug Research, 14, 1-40 (1985).
Davies, et al.; Biochemical Journal, 351, 95-105 (2000).
Gilette, et al.; Biochemistry, 33(10), 2927-2937 (1994).
Gause, et al.; Biodrugs, 15(2), 73-79 (2001).
Kuno, et al.; Blood, 97, 1050-1055 (2001).
Levis, et al.; Blood, 99(11) 3885-3891 (2002).
Gilliand, et al.; Blood, 100(5), 1532-1542 (2002).
Yee, et al.; Blood, 100(8), 2941-2949 (2002).
Tan, et al.; Blood, 104(1), 11-18 (2004).
Kelly, et al.; Cancer Cell, 1, 421-432 (2002).
Weisberg, et al., Cancer Cell, 1, 433-443 (2002).
Jarman, et al.; Carcinogenesis, 16(4), 683-688 (1993).
Khwaja, et al.; Embo, 16(10), 2783-2793 (1997).
Ruzza, et al.; Expert Opinion Therapeutic Patents, 19(10),1361-1376 (2009).
Norman; Expert Opinion Therapeutic Patents, 19(10), 1469-1472 (2009).
Alessi, et al.; FEBS Letter, 399(3), 333-338 (1996).
Chan, et al.; Immunological Review, 169, 107-121 (1999).
Turner, et al.; Immunology Today, 21(3), 148-154 (2000).
Levis, et al.; International Journal of Hematology, 82, 100-107 (2005).
Campos-Gonzalez, et al.; Journal of Biological Chemistry, 267(21), 14535-14538 (1992).
Zou, et al.; Journal of Cell Biology, 176(6), 877-888 (2007).
Marjon, et al.; Journal of Immunology, 182,1397-1403 (2009).
Reeve, et al.; Journal of Immunology,183(3), 1804-1812 (2009).
Combs, et al.; Journal of Neuroscience, 19(3), 928-939 (1999).
Reider, et al.; Journal of Organic Chemistry, 52, 3326-3334 (1987).
Hanzlik, et al.; Journal of Organic Chemistry, 55, 3992-3997 (1990).
Sorg, et al.; Journal of Biomoelecular Screening, 7(1), 11-19 (2002).
Sills, et al.; Journal of Biomeolecular Screening, 7(3), 191-214 (2002).
Klaresklog, et al.; Lancet, 373, 659-672 (2009).
Tomillero, et al.; Methods Find Exp Clin Pharmacol, 31(1), 47-57 (2009).
Taylor, et al.; Molecular and Cellular Biology, 15(8), 4149-4157 (1995).

(Continued)

*Primary Examiner* — Bruck Kifle

(57) ABSTRACT

Compounds of the formula I

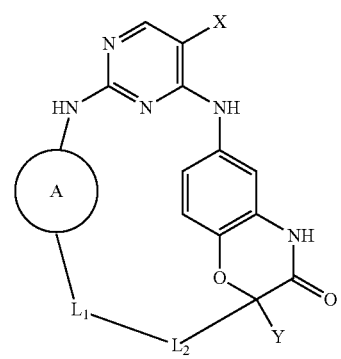

in which A, $L_1$, $L_2$, X and Y have the meanings indicated in Claim 1, are inhibitors of Syk, and can be employed, inter alia, for the treatment of rheumatoid arthritis.

6 Claims, No Drawings

(56) References Cited

OTHER PUBLICATIONS

Frank; Molecular Medicine, 5(7), 432-456 (1999).
Cederbaum, et al.; Molecular Genetics and Metabolism, 81, S38-S44 (2004).
Stirewalt, et al.; Nature Reviews Cancer, 3, 650-665 (2003).
Seidel, et al.; Oncogene, 19, 2645-2656 (2000).
White; Oncogene, 20, 7064-7072 (2001).
Prendergast; Oncogene, 27, 3889-3900 (2008).
Tyle; Pharmaceutical Research, 3(6), 318-326 (1986).
De Santo, et al.; Proc. Nat. Acad. Sci. USA (PNAS), 102(11), 4185-4190 (2005).
Burger's Medicinal Chemistry and Drug Discovery 6th ed. (Donald J. Abraham ed., Wiley) 2001.
Design and Application of Prodrugs (H.Bundgaard ed., Harwood Academic Publishers Gmfh) 1985.

CYCLIC DIAMINOPYRIMIDINE DERIVATIVES

BACKGROUND OF THE INVENTION

The invention had the object of finding novel compounds having valuable properties, in particular those which can be used for the preparation of medicaments.

The present invention relates to compounds and to the use of compounds in which the inhibition, regulation and/or modulation of signal transduction by kinases, in particular tyrosine kinases, furthermore to pharmaceutical compositions which comprise these compounds, and to the use of the compounds for the treatment of kinase-induced diseases.

Because protein kinases regulate nearly every cellular process, including metabolism, cell proliferation, cell differentiation, and cell survival, they are attractive targets for therapeutic intervention for various disease states. For example, cell-cycle control and angiogenesis, in which protein kinases play a pivotal role are cellular processes associated with numerous disease conditions such as but not limited to cancer, inflammatory diseases, abnormal angiogenesis and diseases related thereto, atherosclerosis, macular degeneration, diabetes, obesity, and pain.

One of the key events in the signaling pathway following the activation of mast cells is activation of the tyrosine kinase Syk. Mast cells play a critical role in asthma and allergic disorders by releasing pro-inflammatory mediators and cytokines. Antigen-mediated aggregation of FcεRJ, the high-affinity receptor for IgE, results in activation of mast cells. This triggers a series of signaling events resulting in the release of mediators, including histamine, proteases, leukotrienes and cytokines. These mediators cause increased vascular permeability, mucus production, bronchoconstriction, tissue degradation and inflammation, thus playing key roles in the etiology and symptoms of asthma and allergic disorders. Syk kinase acts as a central initiator of all subsequent signaling leading to mediator release. The critical role of Syk kinase in the signaling path was demonstrated by the complete inhibition of mediator release by a protein containing the SH2 domains of Syk kinase that functioned as an inhibitor of Syk kinase (J. A. Taylor et al, Molec. and Cell Biol, 15: 4149-4157 (1995).

Syk (Spleen-Tyrosine-Kinase) is a 72 kDa non-receptor tyrosine kinase belonging to the subfamily of intracellular tyrosine kinases that comprises ZAP70, Pyk2, Abl, Tie2, KDR and HER, among others. Syk is a major regulator of FcR (FcγRI, II, III, FcεRI, FcαR) and BCR signaling and is expressed throughout hematopoietic lineage, as well as in fibroblasts, osteoclasts, hepatocytes, epithelial and neuronal cells. In addition to the C terminal kinase domain, SYK exhibits two SH2 domains and over 10 autophosphorylation sites[1].

By means of both its SH2 domains SYK is specifically recruited to phosphorylated ITAMs (Immunoreceptor Tyrosine-based Activation Motifs present in immunoreceptors such as FcγRI, IIA, IIIA, FcαR, FcεRI and BCR, expressed by monocytes, macrophages, mast cells, neutrophils and B cells) and specifically mediates immunoreceptor signaling triggered by activation of those receptors in mast cells, B cells, macrophages, monocytes, neutrophils, eosinophils, NK cells, DC cells platelets and osteoclasts[1,2].

Upon BCR cross linking, tyrosine residues at the ITAM motifs of the cytosolic tail of the Igα/Igβ are phosphorylated by the Src-family kinase Lyn, generating docking sites for SYK that is thus recruited to the BCR immunocomplex. SYK is then phosphorylated and activated by the Src-family kinase Lyn. Upon activation, SYK will phosphorylate the adaptor protein BLNK allowing its interaction with both BTK and PLCγ$_2$ via their respective SH2 domains. SYK phosphorylated- and thus activated-BTK will in turn phosphorylate and activate PLCγ$_2$ leading to IP$_3$ formation, Ca$^{2+}$ mobilization, PKC and MAPK activation and consequent NFAT, AP-1 and NFκB transcription factor activation, resulting in activation and surface marker expression, cytokine release, survival and proliferation of B cells[3]. In mast cells, allergen activated FcεRI is phosphorylated by LYN and FYN and recruits SYK which is in turn phosphorylated by LYN and further autophosphorylated, becoming fully activated. Activated SYK phosphorylates the two adaptor molecules NTAL and LAT creating more docking sites for SH2 containing proteins such as PLCγ$_1$, vav, and the p85 regulatory subunit of PI3K, resulting in mast cell degranulation and cytokine production[4]. Syk's critical role in signal transduction of mast cells is confirmed by reproducible observation that the 10-15% of basophils (circulating mast cells) from human donors that cannot degranulate have reduced amounts of Syk protein[5,6]. In addition, SYK is required for the bone resorption activity of osteoclasts. Upon stimulation of osteoclasts by αvβ3 integrin, SYK becomes phosphorylated, most likely by c-Src, in a DAP-12/FcγRII dependent mechanism, leading to SPL-76 and Vav3 phosphorylation and subsequent cytoskeletal reorganisation. SYK deficient osteoclasts are inactive and show defective cytoskeletal reorganisation. In correlation with this, SYK deficient embryos show defective skeletal mass[7,8].

BCR-mediated activation of B-cells in the lymph nodes, as well as FcR-mediated activation of dendritic cells, monocytes, macrophages, neutrophils and mast cells in the joints, are essential components of the cellular patho-physiological mechanisms taking place during rheumaoid arthritis (RA). Moreover, activation of osteoclasts leads to the bone and cartilage destruction which are hallmarks of this pathology[9]. SYK signaling should therefore play a pivotal role during the development of arthritis, both at the periphery and on the site of inflammation[10]. Indeed, an orally available Syk inhibitor R406-developed by Rigel-induced a significant improvement of clinical scores and significantly reduced serum cytokine concentrations, as well as bone erosion, in a murine model of RA[11,12]. Moreover, this inhibitor has shown efficacy (ACR scores improvement) and good tolerability in RA Phase II studies in humans[13,14,15].

In SLE B cells contribute essentially towards pathogenesis via production of autoanibodies resulting in immune complex formation, stimulation of Fc receptors and finally in an excessive and chronic activation of inflammation. In a murine model of SLE treatment with a Syk inhibitor resulted in a reduction of numbers of class-switched germinal center, marginal zone, newly formed and follicular B cells and therefore in disease mitigating effects[18].

Although TCR signals are transmitted by the intracellular tyrosine kinase ZAP-70 in thymocytes and naïve T cells, several studies indicate that differentiated effector T cells, such as those involved in the pathophysiology of Multiple sclerosis (MS) or systemic lupus erythematosus (SLE), show a down regulation of the TCRzeta chain and a concomitant upregulation of the TCR/CD3 chain and its interaction with FcRγ. Those studies show that the TCR/CD3/FcRgamma complex in effector cells recruits and activates Syk, instead of ZAP-70, tyrosine kinase. This physiologic switch in TCR signaling occurs exclusively in effector, and not naive or memory T cells[16,17,18]. Not surprisingly then, SYK inhibitors have been shown to delay disease progression and to improve survival in murine models of SLE[17,18,19,20,21].

SYK inhibitors may also find a use in asthma, allergy, multiple sclerosis and other diseases such as thrombocytopenia purpura and T or B cell lymphomas[1,10,14,22]-35.

Treatment of prediseased NZB/W mice with a Syk inhibitor prevented the development of renal disease demonstrated by reduced glomerular sclerosis, tubular damage, proteinuria and BUN levels[18].

References

1. Turner, M., Schweighoffer, E., Colucci, F., Di Santo, J. P. & Tybulewicz, V. L. Tyrosine kinase SYK: essential functions for immunoreceptor signalling. *Immunol Today* 21, 148-154 (2000).
2. Ghosh, D. & Tsokos, G. C. Spleen tyrosine kinase: an Src family of non-receptor kinase has multiple functions and represents a valuable therapeutic target in the treatment of autoimmune and inflammatory diseases. *Autoimmunity* 43, 48-55.
3. Lindvall, J. M., et al. Bruton's tyrosine kinase: cell biology, sequence conservation, mutation spectrum, siRNA modifications, and expression profiling. *Immunol Rev* 203, 200-215 (2005).
4. Gilfillan, A. M. & Tkaczyk, C. Integrated signalling pathways for mast-cell activation. *Nat Rev Immunol* 6, 218-230 (2006).
5. Gomez, G., Schwartz, L. & Kepley, C. Syk deficiency in human non-releaser lung mast cells. *Clin Immunol* 125, 112-115 (2007).
6. Kepley, C. L., Youssef, L., Andrews, R. P., Wilson, B. S. & Oliver, J. M. Syk deficiency in nonreleaser basophils. *J Allergy Clin Immunol* 104, 279-284 (1999).
7. Zou, W., et al. Syk, c-Src, the alphavbeta3 integrin, and ITAM immunoreceptors, in concert, regulate osteoclastic bone resorption. *J Cell Biol* 176, 877-888 (2007).
8. Reeve, J. L., et al. SLP-76 couples Syk to the osteoclast cytoskeleton. *J Immunol* 183, 1804-1812 (2009).
9. Klareskog, L., Catrina, A. I. & Paget, S. Rheumatoid arthritis. *Lancet* 373, 659-672 (2009).
10. Wong, B. R., Grossbard, E. B., Payan, D. G. & Masuda, E. S. Targeting Syk as a treatment for allergic and autoimmune disorders. *Expert Opin Investig Drugs* 13, 743-762 (2004).
11. Braselmann, S., et al. R406, an orally available spleen tyrosine kinase inhibitor blocks fc receptor signaling and reduces immune complex-mediated inflammation. *J Pharmacol Exp Ther* 319, 998-1008 (2006).
12. Pine, P. R., et al. Inflammation and bone erosion are suppressed in models of rheumatoid arthritis following treatment with a novel Syk inhibitor. *Clin Immunol* 124, 244-257 (2007).
13. Tomillero, A. & Moral, M. A. Gateways to clinical trials. *Methods Find Exp Clin Pharmacol* 31, 47-57 (2009).
14. Bajpai, M. Fostamatinib, a Syk inhibitor prodrug for the treatment of inflammatory diseases. *IDrugs* 12, 174-185 (2009).
15. Weinblatt, M. E., et al. Treatment of rheumatoid arthritis with a Syk kinase inhibitor: a twelve-week, randomized, placebo-controlled trial. *Arthritis Rheum* 58, 3309-3318 (2008).
16. Krishnan, S., Warke, V. G., Nambiar, M. P., Tsokos, G. C. & Farber, D. L. The FcR gamma subunit and Syk kinase replace the CD3 zeta-chain and ZAP-70 kinase in the TCR signaling complex of human effector CD4 T cells. *J Immunol* 170, 4189-4195 (2003).
17. Krishnan, S., et al. Differential expression and molecular associations of Syk in systemic lupus erythematosus T cells. *J Immunol* 181, 8145-8152 (2008).
18. Bahjat, F. R., et al. An orally bioavailable spleen tyrosine kinase inhibitor delays disease progression and prolongs survival in murine lupus. *Arthritis Rheum* 58, 1433-1444 (2008).
19. Smith, J., et al. A Spleen Tyrosine Kinase Inhibitor Reduces the Severity of Established Glomerulonephritis. *J Am Soc Nephrol* (2009).
20. Enyedy, E. J., et al. Fc epsilon receptor type I gamma chain replaces the deficient T cell receptor zeta chain in T cells of patients with systemic lupus erythematosus. *Arthritis Rheum* 44, 1114-1121 (2001).
21. Perl, A. Systems biology of lupus: mapping the impact of genomic and environmental factors on gene expression signatures, cellular signaling, metabolic pathways, hormonal and cytokine imbalance, and selecting targets for treatment. *Autoimmunity* 43, 32-47.
22. Smith, J., et al. A spleen tyrosine kinase inhibitor reduces the severity of established glomerulonephritis. *J Am Soc Nephrol* 21, 231-236.
23. Sanderson, M. P., Gelling, S. J., Rippmann, J. F. & Schnapp, A. Comparison of the anti-allergic activity of Syk inhibitors with optimized Syk siRNAs in FcepsilonRI-activated RBL-2H3 basophilic cells. *Cell Immunol* 262, 28-34.
24. Podolanczuk, A., Lazarus, A. H., Crow, A. R., Grossbard, E. & Bussel, J. B. Of mice and men: an open-label pilot study for treatment of immune thrombocytopenic purpura by an inhibitor of Syk. *Blood* 113, 3154-3160 (2009).
25. Bajpai, M., Chopra, P., Dastidar, S. G. & Ray, A. Spleen tyrosine kinase: a novel target for therapeutic intervention of rheumatoid arthritis. *Expert Opin Investig Drugs* 17, 641-659 (2008).
26. Friedberg, J. W., et al. Inhibition of Syk with fostamatinib disodium has significant clinical activity in non-Hodgkin lymphoma and chronic lymphocytic leukemia. *Blood* 115, 2578-2585.
27. Gao, C., et al. Eptifibatide-induced thrombocytopenia and thrombosis in humans require FcgammaRIIa and the integrin beta3 cytoplasmic domain. *J Clin Invest* 119, 504-511 (2009).
28. Marjon, K. D., Marnell, L. L., Mold, C. & Du Clos, T. W. Macrophages activated by C-reactive protein through Fc gamma RI transfer suppression of immune thrombocytopenia. *J Immunol* 182, 1397-1403 (2009).
29. Chen, L., et al. SYK-dependent tonic B-cell receptor signaling is a rational treatment target in diffuse large B-cell lymphoma. *Blood* 111, 2230-2237 (2008).
30. Ponzoni, M., et al. Syk expression patterns differ among B-cell lymphomas. *Leuk Res* (2010).
31. Pechloff, K., et al. The fusion kinase ITK-SYK mimics a T cell receptor signal and drives oncogenesis in conditional mouse models of peripheral T cell lymphoma. *J Exp Med* 207, 1031-1044 (2009).
32. Uckun, F. M., Ek, R. O., Jan, S. T., Chen, C. L. & Qazi, S. Targeting SYK kinase-dependent anti-apoptotic resistance pathway in B-lineage acute lymphoblastic leukaemia (ALL) cells with a potent SYK inhibitory pentapeptide mimic. *Br J Haematol* 149, 508-517 (2010).
33. Wilcox, R. A., et al. Inhibition of Syk protein tyrosine kinase induces apoptosis and blocks proliferation in T-cell non-Hodgkin's lymphoma cell lines. *Leukemia* 24, 229-232 (2009).

34. Feldman, A. L., et al. Overexpression of Syk tyrosine kinase in peripheral T-cell lymphomas. *Leukemia* 22, 1139-1143 (2008).
35. Wang, L., et al. Alternative splicing disrupts a nuclear localization signal in spleen tyrosine kinase that is required for invasion suppression in breast cancer. *Cancer Res* 63, 4724-4730 (2003).

In addition to mast cells, Syk is expressed in other hematopoietic cells including B cells, where it is thought to play an essential role in transducing signals required for the transition of immature B cells into mature recirculating B cells (M. Turner et al, Immunology Today, 21: 148 (2000). B cells are reported to play an important role in some inflammatory conditions such as lupus (O. T. Chan et al., Immunological Rev, 169: 107-121 (1999) and rheumatoid arthritis (A. Gause et al, Biodrugs, 15(2): 73-79 (2001).

Syk was also reported to be an element of the signaling cascade in beta-amyloid and prion fibrils leading to production of neurotoxic products (C. K. Combs et al., J. Neuroscl, 19: 928-939 (1999). Furthermore, an inhibitor of Syk blocked the production of these neurotoxic products. Thus furopyridine derivatives would potentially be useful in the treatment of Alzheimer's disease and related neuroinflammatory diseases. Another report (Y. Kuno et al., Blood, 97, 1050-1055 (2001) demonstrates that Syk plays an important role in malignant progression. A TEL-Syk fusion protein was found to transform hematopoietic cells suggesting a role in the pathogenesis of hematopoietic malignancies. Therefore furopyridine derivatives may be useful in the treatment of certain types of cancers.

Other protein tyrosine kinases involved in hematologic malignancies include ABL (ABLI), ARG (ABL2), PDGFβR, PDGFaR, JAK2, TRKC, FGFRI, FGFR3, FLT3, and FRK.

The Janus kinases (JAK) are a family of tyrosine kinases consisting of JAKI, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas (for a review of the pharmaceutical intervention of the JAK/STAT pathway see Frank, Mol. Med. 5, 432:456 (1999), and Seidel et al, Oncogene 19, 2645-2656 (2000). JAK2 is a well validated target with strong potential in the treatment of myeloproliferative disorders (MPDs), which include polycythemia vera (PV), essential thrombocythemia, chronic idiopathic myelofibrosis, myeloid metaplasia with myelofibrosis, chronic myeloid leukemia, chronic myelomonocytic leukemia, chronic eosinophilic leukemia, hypereosinophilic syndrome and systematic mast cell disease.

Fms-like tyrosine kinase 3 (FLT3), which is also known as FLK-2 (fetal liver kinase 2) and STK-I (stem cell kinase 1), plays an important role in the proliferation and differentiation of hematopoietic stem cells. FLT3 receptor kinase is expressed in normal hematopoietic cells, placenta, gonads, and brain. However, this enzyme is expressed at very high levels on the cells of more than 80% of myelogenous patients and of a fraction of acute lymphoblastic leukemia cells. Furthermore, the enzyme can also be found on cells from patients with chronic myelogenous leukemia in lymphoid blast crisis. It has been reported that FLT3 kinase is mutated in 30% of acute myeloid leukemia (AML) and in a subset of acute lymphoblastic leukemia (ALL) as well (Gilliland et al, Blood 100, 1532-1542 (2002); Stirewalt et al, Nat. Rev. Cancer, 3, 650-665 (2003). The most common activating mutations in FLT3 are internal tandem duplications within the juxtamembrane region, while point mutations, insertions, or deletions in the kinase domain are less common. Some of these mutant FLT3 kinases are constitutively active. FLT3 mutations have been associated with a poor prognosis (Malempati et al., Blood, 104, 11 (2004). More than a dozen known FLT3 inhibitors are being developed and some have shown promising clinical effects against AML (Levis et al Int. J. Hematol, 52, 100-107 (2005).

It has been reported that some of small-molecule FLT3 inhibitors are effective in inducing apoptosis in cell lines with FLT3-activating mutations and prolonging survival of mice that express mutant FLT3 in their bone marrow cells (Levis et al, Blood, 99, 3885-3891 (2002); Kelly et al, Cancer Cell, 1, 421-432 (2002); Weisberg et al, Cancer Cell, 1, 433-443 (2002); Yee et al, Blood, 100, 2941-2949 (2002).

In particular, the present invention relates to compounds and to the use of compounds in which the inhibition, regulation and/or modulation of signal transduction by Syk plays a role.

The synthesis of small compounds which specifically inhibit, regulate and/or modulate signal transduction by tyrosine kinases in particular Syk, is therefore desirable and an aim of the present invention.

Moreover, aim of this invention is the synthesis of new compounds for the prevention and treatment of rheumatoid arthritis, systemic lupus, asthma, allergic rhinitis, ITP, multiple sclerosis, leukemia, breast cancer and maligna melanoma. Surprisingly we have identified furopyridines that inhibit selectively SYK, BTK, KDR, Src, Zap70, Fak, Pyk2, Flt3 or Jak or inhibit a selection of these kinases.

Moreover, compounds of formula I inhibit serin kinase GCN2.

Many strategies of cancer treatment of solid tumors focus on the surgically removal of the tumor mass as far as possible and the subsequent eradication of any residual tumor cells by radiotherapy and chemotherapy with cytotoxic agents or inhibitors that target cancer cell pathways more specifically. However, the success of such approach is limited and often does not persist. This is mainly due to the narrow therapeutic window for such cytotoxic agents (specificity and side effects) and to the capability of cancer calls to adapt to the selective pressure applied by cytotoxic or other inhibitory agents. The survival of a small number of tumor (stem) cells that acquired resistance to the initial treatment can be sufficient to seed the regrowth of a tumor. These relapses are in most cases more difficult to treat compared to that of the initial tumors. As a consequence the more successful targeting of tumor cells may require targeting multiple survival and escape mechanism of tumor cells in parallel (Muller & Prendegast 2007).

Development of malignancies is accompanied by a major roll up of the cellular physiology. During this process several qualities are acquired by the cancer cells that are basis for immortalization or insensitivity to growth inhibitory signals. In addition the tumor cells also modify the interaction with the microenvironment and beyond. The latter area includes the strategies of tumor cells to escape from the immunological surveillance (Muller & Prendegast 2007). The immune surveillance limits malignant growth but also provides a selective pressure triggering the evolution of mechanisms for evading the immune response as reviewed by [Dunn et al. 2004]. Essentially it has been frequently observed that ablation of T cell immunity is sufficient to increase tumor incidence [Shankaran et al. 2001] and it is believed that immune escape is affecting tumor dormancy versus progression, promoting invasion and metastasis and negatively impacts on therapeutic response. Several mechanistic studies discovered that immune escape has an important interface with metabolic alterations within the tumor microenvironment. Here important roles in mediating immune tolerance to antigens have been associated to the catabolism of the essential amino acids tryptophan and arginine, carried out by the enzymes indoleamine 2,3-dioxygenase (IDO) and arginase I (ARG), respectively (Bronte and Zanovello, 2005; Muller et al., 2005b; Muller and Prendergast, 2007; Munn and Mellor, 2007; Popovic et al., 2007).

IDO is a single-chain oxidoreductase that catalyzes the degradation of tryptophan to kynurenine. IDO is not responsible for catabolizing excess dietary tryptophan but to modulate tryptophan level in a local environment. Elevations in tryptophan catabolism in cancer patients manifest in significantly altered serum concentration of tryptophan or catabolites and this was correlated to IDO which is commonly elevated in tumors and draining lymph nodes. According to several publications IDO over-expression is associated with poor prognosis in cancer [Okamoto et al 2005; Brandacher et al, 2006].

T cells appear to be preferentially sensitive to IDO activation, such that when starved for tryptophan they cannot divide and as a result cannot become activated by an antigen presented to them. Munn and Mellor and their colleagues, revealed that IDO modulates immunity by suppressing T-cell activation and by creating peripheral tolerance to tumor antigens (Mellor and Munn, 2004). These mechanism encompass the subversion of immune cells recruited by the tumor cell to its immediate microenvironment or to the tumor-draining lymph nodes Here the tumor antigens that were scavenged by antigen-presenting cells are cross-presented to the adaptive immune system. In addition to being directly toleragenic, mature DCs have the capacity to expand regulatory Tcells (Tregs) [Moser 2003].

Beside tryptophan catabolism the conversion of arginine is increased in a tumor-conditioned microenvironment, and numerous reports indicate a role for the activation of arginases during tumor growth and development. In tumor-infiltrating myeloid cells, arginine is converted by arginase I (ARG1), arginase II (ARG2) to urea and ornithine and oxidized by the inducible form of nitric oxide synthase (NOS2) to citrulline and nitric oxide (NO).

Increased ARG activity is frequently observed in patients with colon, breast, lung, and prostate cancer [Cederbaum 2004] correlating with the over-expression of ARG and NOS found in prostate cancers [Keskinege et al. 2001, Aaltoma et al. 2001, Wang et al. 2003]. It was shown that ARG activity in infiltrating macrophages impairs antigen-specific T cell responses and the expression of the CD3 receptor. Moreover the cumulative activity of ARG and NOS in tumor associated myeloid cells can generate inhibitory signals to antigen-specific T lymphocytes that eventually lead to apoptosis [Bronte 2003 a; 2003b].

Both, the IDO and the ARG related mechanism merge at the point of sensing the depleted concentration of the respective amino acid concentration. During amino acid deprivation, the eIF2 kinase EIF2AK4 called general control nonderepressible 2 (GCN2) is interacting with the intracellular accumulating deacylated tRNA. As a consequence the GCN2 is assumed to change from an auto-inhibited to an active conformation and further activate by auto-phosphorylation. Then the only known substrate protein eIF2a becomes phosphorylated and as a consequence the complex for translation initiation is inhibited [Harding et al. 2000]. This diminishes the general Cap-dependent translation initiation and by this the corresponding protein production. On the other hand this induces the specific expression of stress related target genes mainly by cap-independent initiation via the activating transcription factor 4 (ATF4). By expressing the respective stress response proteins, e.g. enzymes in the in amino acid metabolism, the cell tries to compensate the particular cell stress [Wek et al. 2006]. If the stress persists, the same pathway will switch to promoting cell death via transcription of the pro-apoptotic transcription factor, CCAAT/enhancer-binding protein homologous protein (CHOP) [Oyadomari 2004]. It was shown that, tryptophan starvation triggers a GCN2-dependent stress signaling pathway In T cells altering eIF2aphosphorylation and translational initiation leading to a cell growth arrest (Munn et al. 2005). Sharma, et al. [2007] published on the direct IDO-induced and GCN2-dependent activation of mature Tregs. Similarly Fallarino et al [2006] found a GCN2-dependent conversion of CD4+CD25− cells to CD25+FoxP3+ Tregs producing IL-10 and TGF. Rodriguez et al. [2007] identified that activation of the GCN2 pathway via tryptophan or arginine depletion in combination with TCR signaling leads to CD3 chain down regulation, cell cycle arrest and anergy.

Importantly the GCN2 pathway is not only important for the tumoral immune escape but also plays an active role in modulating tumor survival directly. Ye et al [2010] found that the aforementioned transcription factor ATF4 is over-expressed inhuman solid tumors, suggesting an important function in tumour progression. Amino acid and glucose deprivation are typical stresses found in solid tumours and activated the GCN2 pathway to up-regulate ATF4 target genes involved in amino acid synthesis and transport. GCN2 activation/overexpression and increased phospho-eIF2a were observed in human and mouse tumors compared with normal tissues and abrogation of ATF4 or GCN2 expression significantly inhibited tumor growth in vivo. It was concluded that the GCN2-eIF2a-ATF4 pathway is critical for maintaining metabolic homeostasis in tumor cells.

Over all the present biology makes an interference with the ARG/IDO pathway attractive for braking up the tumoral immune escape by adaptive mechanism. The interference of GCN2 function is here of particular interest as it is a merging point of the two pathways, the IDO and ARG, as well as it provides additional opportunities to impede with the tumor metabolism directly.

Several pathway inhibitors are already considered as immune modulators. These inhibitors address mainly the enzymatic function of the IDO or ARG proteins (Muller and Scherle, 2006). The application of the arginase inhibitor, N-hydroxy-nor-L-Arg blocks growth of s.c. 3LL lung carcinoma in mice [Rodriguez 2004]. The NO-donating aspirins like NCX 4016 (2-(acetyloxy)benzoic acid 3-(nitrooxymethyl) phenyl ester) have been reported to interfer with the inhibitory enzymatic activities of myeloid cells. Orally administered NO aspirin normalized the immune status of tumor-bearing hosts, increased the number and function of tumor-antigen-specific T lymphocytes, and enhanced the preventive and therapeutic effectiveness of the antitumor immunity elicited by cancer vaccination (DeSanto 2005)

The substrate analogue 1 methyl-tryptophan (1 MT) and related molecules have been used widely to target IDO in the cancer context and other settings. Studies by Friberg et al. (2002) and Uyttenhove et al. (2003) demonstrated that 1 MT can limit the growth of tumors over-expressing IDO. However 1 MT was unable to elicit tumor regression in several tumor models, suggesting only modest antitumor efficacy when IDO inhibition was applied as a monotherapy. In contrast, the combinatory treatment with 1 MT and a variety of cytotoxic chemotherapeutic agents elicited regression of established MMTV-neu/HER2 tumors, which responded poorly to any single-agent therapy [Muller et al 2005a]. Immunodepletion of CD4+ or CD8+ T cells from the mice, before treatment abolished the combinatorial efficacy observed in this model, confirming the expectation that 1 MT acted indirectly through activation of T cell-mediated antitumor immunity. Important evidence that IDO targeting is essential to 1 MT action was provided by the demonstration that 1 MT lacks antitumor activity in mice that are genetically deficient for IDO [Hou et al., 2007] The inhibition of GCN2 would enable to combine the two pathway branches of amino acrid starvation induced immunoediting and would reduce the options for the tumor to circumvent the inhibition of either branch. Moreover, as detailed above, the GCN2 inhibition provides the opportunity for interfering with the tumor metabolism at the same time what may enhance the efficacy of a monotherapy or a combination therapy with other anti-cancer approaches.

Literature

1. Aaltoma, S. H., P. K. Lipponen, and V. M. Kosma. 2001. Inducible nitric oxide synthase (iNOS) expression and its prognostic value in prostate cancer. Anticancer Res. 21:3101-3106.
2. Brandacher, G.; Perathoner, A.; Ladurner, R.; Schneeberger, S.; Obrist, P.; Winkler, C.; Werner, E. R.; Werner-Felmayer, G.; Weiss, H. G.; Gobel, G.; Margreiter, R.; Konigsrainer, A.; Fuchs, D.; Amberger, A. Prognostic value of indoleamine 2,3-dioxygenase expression in colorectal cancer: effect on tumorinfiltrating T cells. Clin. Cancer Res. 2006, 12, 1144-1151.
3. Bronte V, Zanovello P. (2005). Regulation of immune responses by L-arginine metabolism. Nat Rev Immunol 5: 641-654.
4. Bronte, V., P. Serafini, C. De Santo, I. Marigo, V. Tosello, A. Mazzoni, D. M. Segal, C. Staib, M. Lowel, G. Sutter, et al. 2003a. IL-4-induced arginase 1 suppresses alloreactive T cells in tumor-bearing mice. J. Immunol. 170:270-278.
5. Bronte, V., P. Serafini, A. Mazzoni, D. M. Segal, and P. Zanovello. 2003b. L-arginine metabolism in myeloid cells controls T-lymphocyte functions. Trends Immunol. 24:302-306
6. Carmela De Santo, Paolo Serafini, Ilaria Marigo, Luigi Dolcetti, Manlio Bolla, § Piero Del Soldato, Cecilia Melani, Cristiana Guiducci, Mario P. Colombo, Manuela Iezzi, Piero Musiani, Paola Zanovello, and Vincenzo Bronte. Nitroaspirin corrects immune dysfunction in tumor-bearing hosts and promotes tumor eradication by cancer vaccination. Proc Natl Acad Sci USA. 2005 March 15; 102(11): 4185-4190
7. Cederbaum, S. D., H. Yu, W. W. Grody, R. M. Kern, P. Yoo, and R. K. Iyer. 2004. Arginases I and II: do their functions overlap? Mol. Genet. Metab. 81:S38-44.
8. Dey, M., Cao, C., Sicheri, F. and T. E. Dever. Conserved Intermolecular Salt Bridge Required for Activation of Protein Kinases PKR, GCN2, and PERK. JBC 282(9): 6653, 2007.
9. Dunn, G. P.; Old, L. J.; Schreiber, R. D. The immunobiology of cancer immunosurveillance and immunoediting. Immunity 2004, 21, 137-148.
10. Fallarino, F. U. Grohmann, S. You, B. C. et al. The combined effects of tryptophan starvation and tryptophan catabolites down-regulate T cell receptor zeta-chain and induce a regulatory phenotype in naïve T cells. J. Immunol. 176:6752, 2006.
11. Friberg M, Jennings R, Alsarraj M, Dessureault S, Cantor A, Extermann M et al. (2002). Indoleamine 2,3-dioxygenase contributes to tumor cell evasion of T cell-mediated rejection. Int. J. Cancer 101: 151-155
12. Harding H P, Novoa I, Zhang Y, Zeng H, Wek R, Schapira M, Ron D. Regulated translation initiation controls stress-induced gene expression in mammalian cells. Mol. Cell. 2000 November; 6(5):1099-108.
13. Hou D Y, Muller A J, Sharma Md., DuHadaway J, Banerjee T, Johnson M et al. (2007). Inhibition of indoleamine 2,3-dioxygenase in dendritic cells by stereoisomers of 1-methyl-tryptophan correlates with antitumor responses. Cancer Res 67: 792-801.
14. Keskinege, A., S. Elgun, and E. Yilmaz. 2001. Possible implications of arginase and diamine oxidase in prostatic carcinoma. Cancer Detect. Prey. 25:76-79.
15. Mellor A L, Munn D H. (2004). IDO expression by dendritic cells: tolerance and tryptophan catabolism. Nat Rev Immunol 4: 762-774.
16. Moser, M. Dendritic cells in immunity and tolerance-do they display opposite functions? Immunity 2003, 19, 5-8.
17. Muller, A. J. and P. A. Scherle. Targeting the mechanisms of tumoral immune tolerance with small-molecule inhibitors. Nat. Rev. Cancer. 6:613, 2006.
18. Muller A J, Prendergast G C. (2007). Indoleamine 2,3-dioxygenase in immune suppression and cancer. Curr Cancer Drug Targets 7: 31-40.
19. Muller A J, DuHadaway J B, Sutanto-Ward E, Donover P S, Prendergast G C. (2005a). Inhibition of indoleamine 2,3-dioxygenase, an immunomodulatory target of the tumor suppressor gene Bin1, potentiates cancer chemotherapy. Nature Med 11: 312-319.
20. Muller A J, Malachowski W P, Prendergast G C. (2005b). Indoleamine 2,3-dioxygenase in cancer: targeting pathological immune tolerance with small-molecule inhibitors. Expert Opin Ther Targets 9: 831-849.
21. Munn, D. H., M. D. Sharma, B. Baban, H. P. Harding, Y. Zhang, D. Ron, A. L. Mellor. GCN2 kinase in T cells mediates proliferative arrest and anergy induction in response to indoleamine 2,3-dioxygenase. Immunity. 22:633, 2005
22. Okamoto, A.; Nikaido, T.; Ochiai, K.; Takakura, S.; Saito, M.; Aoki, Y.; Ishii, N.; Yanaihara, N.; Yamada, K.; Takikawa, O.; Kawaguchi, R.; Isonishi, S.; Tanaka, T.; Urashima, M. Indoleamine 2,3-dioxygenase serves as a marker of poor prognosis in gene expression profiles of serous ovarian cancer cells. Clin. Cancer Res. 2005, 11, 6030-6039.
23. Oyadomari S, Mori M. Roles of CHOP/GADD153 in endoplasmic reticulum stress. Cell Death Differ. 2004 April; 11(4):381-9.
24. G C Prendergast, Immune escape as a fundamental trait of cancer: focus on IDO. Oncogene (2008) 27, 3889-3900
25. Popovic P J, Zeh III H J, Ochoa J B. (2007). Arginine and immunity. J Nutr 137: 1681S-1686 S.
26. Rodriguez, P. C., D. G. Quiceno, J. Zabaleta, B. Ortiz, A. H. Zea, M. B. Piazuelo, A. Delgado, P. Correa, J. Brayer, E. M. Sotomayor, S. Antonia, J. B. Ochoa, and A. C. Ochoa. Arginase I Production in the Tumor Microenvironment by Mature Myeloid Cells Inhibits T-Cell Receptor Expression and Antigen-Specific T-Cell Responses. Canc. Res. 64:5839, 2004

27. Rodriguez, P. C., D. G. Quiceno, and A. C. Ochoa. L-arginine availability regulates T-lymphocyte cell-cycle progresión. Blood. 109:1568, 2007.
28. Shankaran, V.; Ikeda, H.; Bruce, A. T.; White, J. M.; Swanson, P. E.; Old, L. J.; Schreiber, R. D. IFNgamma and lymphocytes prevent primary tumour development and shape tumour immunogenicity. Nature 2001, 410, 1107-1111.
29. Sharma, M. D., B. Baban, P. Chandler, D-Y. Hou, N. Singh, H. Yagita, M. Azuma, B. R. Blazar, A. L. Mellor, and D. H. Munn. Plasmacytoid dendritic cells from mouse tumor-draining lymph nodes directly activate mature Tregs via indoleamine 2,3-dioxygenase. J. Clin. Invest. 117:2570, 2007.
30. Uyttenhove C, Pilotte L, Theate I, Stroobant V, Colau D, Parmentier N et al. (2003). Evidence for a tumoral immune resistance mechanism based on tryptophan degradation by indoleamine 2,3-dioxygenase. Nat Med 9: 1269-1274
31. Wang, J., M. Torbenson, Q. Wang, J. Y. Ro, and M. Becich. 2003. Expression of inducible nitric oxide synthase in paired neoplastic and non-neoplastic primary prostate cell cultures and prostatectomy specimen. Urol. Oncol. 21:117-122.
32. Wek R C, Jiang H Y, Anthony T G. Coping with stress: eIF2 kinases and translational control. Biochem Soc Trans. 2006 February; 34 (Pt 1):7-11.
33. Ye J, Kumanova M, Hart L S, Sloane K, Zhang H, De Panis D N, Bobrovnikova-Marjon E, Diehl J A, Ron D, Koumenis C. The GCN2-ATF4 pathway is critical for tumour cell survival and proliferation in response to nutrient deprivation. EMBO J. 2010 Jun. 16; 29(12):2082-96.

It has been found that the compounds according to the invention and salts thereof have very valuable pharmacological properties while being well tolerated.

The present invention specifically relates to compounds of the formula I which inhibit, regulate and/or modulate signal transduction by Syk, to compositions which comprise these compounds, and to processes for the use thereof for the treatment of Syk-induced diseases and complaints.

The compounds of the formula I can furthermore be used for the isolation and investigation of the activity or expression of Syk. In addition, they are particularly suitable for use in diagnostic methods for diseases in connection with unregulated or disturbed Syk activity.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow active agents such as anti IgM to induce a cellular response such as expression of a surface marker, usually between about one hour and one week. In vitro testing can be carried out using cultivated cells from blood or from a biopsy sample. The amount of surface marker expressed are assessed by flow cytometry using specific antibodies recognising the marker.

The dose varies depending on the specific compound used, the specific disease, the patient status, etc. A therapeutic dose is typically sufficient to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-Gonzalez, R. and Glenney, Jr., J. R. 1992, J. Biol. Chem. 267, page 14535).

For the identification of kinase inhibitors, various assay systems are available. In scintillation proximity assay (Sorg et al., J. of. Biomolecular Screening, 2002, 7, 11-19) and flash-plate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214).

Other non-radioactive ELISA assay methods use specific phospho-antibodies (phospho-ABs). The phospho-AB binds only the phosphorylated substrate. This binding can be detected by chemiluminescence using a second peroxidase-conjugated anti-sheep antibody (Ross et al., 2002, Biochem. J.).

Prior Art

Other macrocyclic pyrimidine derivatives are disclosed as aurora kinase inhibitors in WO 2010/028116 A1.

SUMMARY Of THE INVENTION

The invention relates to compounds of the formula I

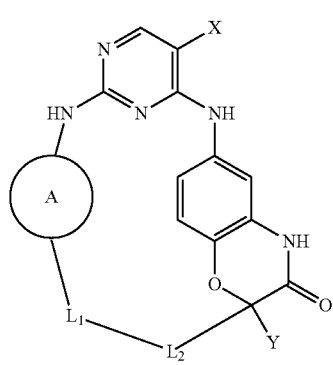

in which (A)

denotes phenylen or 2,3-dihydro-indol-1,6-diyl, each of which is unsubstituted or monosubstituted by OA, X denotes Hal, Y denotes alkyl having 1, 2, 3 or 4 C atoms, $L_1$ denotes $(CH_2)_p NR^1 CO$, $(CH_2)_n$, $NH(CH_2)_n$, $OCH_2 CHOH$, $NHCO(CH_2)_n$, $CO(CH_2)_n NR^1$, $CONR^2$, $(CH_2)_n CONR^1$, $O(CH_2)_p CONR^1$, $NR^1 CONR^3 CHR^4 CONR^1$, $SO_2 NR^1 (CH_2)_p CONR^1$ or $O(CH_2)_p NR^1 CO$, $L_2$ denotes $O(CH_2)_p$, $(CH_2)_n NR^1 CO$, $O(CH_2)_p NR^1 CO$, $CHR^5 NR^1 CO$ or $CHR^3 NR^4 CO$, $R^1$ denotes H or methyl, $R^2$ denotes piperidinyl, piperazinyl, pyrrolidinyl, morpholinyl, 2,3-dihydro-pyrazolyl, 1,2-dihydro-pyridyl or tetrahydropyranyl, each of which is unsubstituted or mono- or disubstituted by A and/or =O, $R^3$ and $R^4$ together denote an alkylene chain having 2, 3 or 4 $CH_2$ groups, $R^5$ denotes A or benzyl, A denotes unbranched or branched alkyl having 1-10 C atoms, in which 1-7 H atoms may be replaced by F and/or in which one or two non-adjacent CH and/or $CH_2$ groups may be replaced by O or N, Hal denotes F, Cl, Br or I, n denotes 0, 1, 2, 3 or 4, p denotes 1, 2, 3 or 4, and pharmaceutically usable solvates, salts, tautomers and stereoisomers thereof, including mixtures thereof in all ratios.

The invention also relates to the optically active forms (stereoisomers), the enantiomers, the racemates, the diastereomers and the hydrates and solvates of these compounds.

Moreover, the invention relates to pharmaceutically acceptable derivatives of compounds of formula I.

The term solvates of the compounds is taken to mean adductions of inert solvent molecules onto the compounds which form owing to their mutual attractive force. Solvates are, for example, mono- or dihydrates or alcoholates. The term pharmaceutically acceptable derivatives is taken to mean, for example, the salts of the compounds according to the invention and also so-called prodrug compounds.

As used herein and unless otherwise indicated, the term "prodrug" means a derivative of a compound of formula I that can hydrolyze, oxidize, or otherwise react under biological conditions (in vitro or in vivo) to provide an active compound, particularly a compound of formula I. Examples of prodrugs include, but are not limited to, derivatives and metabolites of a compound of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers Gmfh).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence: improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function. The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution.

The invention relates to the compounds of the formula I and salts thereof and to a process for the preparation of compounds of the formula I and pharmaceutically usable salts, solvates, tautomers and stereoisomers thereof, characterised in that characterised in that a compound of the formula II

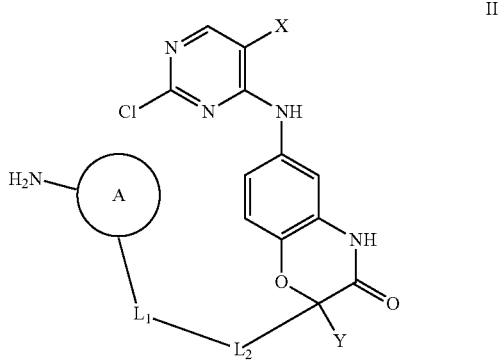

II in which (A), $L_1$, $L_2$, X and Y have the meanings indicated in claim 1, is cyclized, and/or a base or acid of the formula I is converted into one of its salts.

Above and below, the radicals (A), $L_1$, $L_2$, X and have the meanings indicated for the formula I, unless expressly stated otherwise.

A denotes alkyl, this is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl. A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl. Moreover, A denotes e.g. $CH_2OCH_3$, $CH_2CH_2OH$, $OCH_2CH_2NH_2$, $CH_2NHCH_3$ or $NHCH_2CH_3$.

$$\boxed{A}$$

preferably denotes 1,3- or 1,4-phenylen or 2,3-dihydro-indol-1,6-diyl, each of which is unsubstituted or monosubstituted by OA.

Y particularly preferably denotes methyl.

$R^2$ particularly preferably denotes piperidinyl or pyrrolidinyl, each of which is unsubstituted or monosubstituted by A.

Hal preferably denotes F, Cl or Br, but also I, particularly preferably F or Cl. Throughout the invention, all radicals which occur more than once may be identical or different, i.e. are independent of one another.

The compounds of the formula I may have one or more chiral centres and can therefore occur in various stereoisomeric forms. The formula I encompasses all these forms.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise Use can also be made here of variants known per se which are not mentioned here in greater detail.

The starting compounds of the formulae II known. If they are novel, however, they can be prepared by methods known per se.

Compounds of the formula I can preferably be obtained by cyclizing a compound of the formula II.

Depending on the conditions used, the reaction time is between a few minutes and 14 days, the reaction temperature is between about −30° and 140°, normally between 0° and 100°, in particular between about 60° and about 90°. Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to acetonitrile, dimethylformamide, trifluoracetic acid and/or mixtures thereof.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxy group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogen-phosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction. Compounds of the present invention which contain basic nitrogen-containing groups can be quaternised using agents such as $(C_1-C_4)$alkyl halides, for example methyl, ethyl, isopropyl and tert-butyl chloride, bromide and iodide; di$(C_1-C_4)$alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Isotopes

There is furthermore intended that a compound of the formula I includes isotope-labelled forms thereof. An isotope-labelled form of a compound of the formula I is identical to this compound apart from the fact that one or more atoms of the compound have been replaced by an atom or atoms having an atomic mass or mass number which differs from the atomic mass or mass number of the atom which usually occurs naturally. Exam-pies of isotopes which are readily commercially available and which can be incorporated into a compound of the formula I by well-known methods include isotopes of hydrogen, carbon, nitrogen, oxygen, phos-phorus, fluo-rine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively.

A compound of the formula I, a prodrug, thereof or a pharmaceutically acceptable salt of either which contains one or more of the above-mentioned isotopes and/or other isotopes of other atoms is intended to be part of the present invention. An isotope-labelled compound of the formula I can be used in a number of beneficial ways. For example, an isotope-labelled compound of the formula I into which, for example, a radioisotope, such as $^3H$ or $^{14}C$, has been incorporated is suitable for medicament and/or substrate tissue distribution assays. These radioisotopes, i.e. tritium ($^3H$) and carbon-14 ($^{14}C$), are particularly preferred owing to simple preparation and excellent detectability. Incor-po-ra-tion of heavier isotopes, for example deuterium ($^2H$), into a compound of the formula I has therapeutic advantages owing to the higher metabolic stability of this isotope-labelled compound. Higher metabolic stability translates directly into an increased in vivo half-life or lower dosages, which under most circumstances would represent a preferred embodiment of the present invention. An isotope-labelled compound of the formula I can usually be prepared by carrying out the procedures dis-closed in the synthesis schemes and the related description, in the example part and in the preparation part in the present text, replacing a non-isotope-labelled reactant by a readily available isotope-labelled reactant.

Deuterium ($^2H$) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus cause a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a com-pound of the formula I that is susceptible to oxidation, the profile of this compound in vivo can be drastically modified and result in improved pharmacokinetic properties.

When discovering and developing therapeutic agents, the person skilled in the art attempts to optimise pharmacokinetic parameters while retaining desirable in vitro properties. It is reasonable to assume that many com-pounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative meta-bolism. Significant improvements in the pharmacokinetic profiles of compounds of the formula I are thereby obtained, and can be expressed quantitatively in terms of increases in the in vivo half-life (t/2), concen-tra-tion at maximum therapeutic effect ($C_{max}$), area under the dose response curve (AUC), and F; and in terms of reduced clearance, dose and materi-als costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent of the extent to which the improve-ment in resistance to oxidative metabolism has improved. In this way, it is deter-mined that the half-life of the parent compound can be extended by up to 100% as the result of deuterium-hydrogen exchange of this type.

Deuterium-hydrogen exchange in a compound of the formula I can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

The invention furthermore relates to medicaments comprising at least one compound of the formula I and/or pharmaceutically acceptable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be en-capsulated in microcapsules. The formulation can also be prepared in such a way that the release is extended or retarded, such as, for example, by coating or embedding of particulate material in polymers, wax and the like.

The compounds of the formula I and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates and physiologically functional derivatives thereof can also be delivered using monoclonal antibodies as individual carriers to which the compound molecules are coupled.

The compounds can also be coupled to soluble polymers as targeted medicament carriers. Such polymers may encompass polyvinylpyrrolidone, pyran copolymer, polyhydroxypropylmethacrylamidophenol, polyhydroxy-ethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The disclosed compounds of the formula I can be administered in combination with other known therapeutic agents including agents for the treatment of RA (rheumatoid arthritis). As used here, the term "agents for the treatment of RA" relates to any agent which is administered to a patient with RA for the purposes of treating the RA.

The medicaments below are preferably, but not exclusively, combined with the compounds of the formula I:
1. NSAIDs (non-steroidal anti-inflammatory drugs) and analgesics
2. Glucocorticoids (low oral doses)
3. Conventional disease-modifying antirheumatic drugs (DMARDs)
   Methotrexate
   Leflunomide
   Sulfasalazine
   Hydroxycloroquine
   Azathioprine
   Ciclosporin
   Minocycline
   Gold
4. Biologic response modifiers (BRMs)->target molecules/immune cells involved in the inflammatory process, and include the following agents:
   TNF inhibitors
      etanercept (Enbrel)
      infliximab (Remicade)
      adalimumab (Humira)
   B-cell-directed therapy
      rituximab (Rituxan)
   T-cell/B-cell coactivation signal inhibitor
      abatacept (Orencia)
   IL-1 receptor antagonist
      anakinra (Kineret)

| | MECHANISM OF ACTION |
|---|---|
| Golimumab | Fully humanized monoclonal antibody to TNF |
| Certolizumab pegol | Anti-TNF agent with just the Fab portion attached to the polyethylene glycol |
| Tocilizumab | Humanized monoclonal anti-IL-6 antibody that binds to the soluble and membrane-expresses IL-6 receptor |
| Ocrelizumab | Humanized-second generation anti-CD20 antibody that depletes B cells |
| Ofatumumab | Human monoclonal anti-CD20 IgG1 antibody |
| Denosumab | Fully humanized monoclonal antibody that binds to and inhibits the receptor activator for nuclear factor-kB ligand |
| TRU-015 | New class of CD20-directed protein therapeutics |
| Oral small molecules (JAK, Syk, MAP kinase inhibitors) | Cytoplasmic targets |
| Tolerogens (dnaJP1) | Immunotherapy based on T-cell tolerization |

A combined treatment of this type can be achieved with the aid of simultaneous, consecutive or separate dispensing of the individual components of the treatment. Combination products of this type employ the compounds according to the invention.

The invention furthermore relates to medicaments comprising at least one compound of the formula I and/or pharmaceutically acceptable salts, solvates and stereoisomers thereof, including mixtures thereof in all ratios, and at least one further medicament active ingredient.

The invention furthermore relates to a pharmaceutical composition comprising a compound of formula I according to claim 1, and a physiologically acceptable carrier, diluent, or excipient.

The invention also relates to a set (kit) consisting of separate packs of
(a) an effective amount of a compound of the formula I and/or pharmaceutically acceptable salts, solvates and stereoisomers thereof, including mixtures thereof in all ratios, and
(b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically acceptable salts, solvates and stereoisomers thereof, including mixtures thereof in all ratios, and an effective amount of a further medicament active ingredient in dissolved or lyophilised form.

"Treating" as used herein, means an alleviation, in whole or in part, of symptoms associated with a disorder or disease, or slowing, or halting of further progression or worsening of those symptoms, or prevention or prophylaxis of the disease or disorder in a subject at risk for developing the disease or disorder.

The term "effective amount" in connection with a compound of formula (I) can mean an amount capable of alleviating, in whole or in part, symptoms associated with a disorder or disease, or slowing or halting further progression or worsening of those symptoms, or preventing or providing prophylaxis for the disease or disorder in a subject having or at risk for developing a disease disclosed herein, such as inflammatory conditions, immunological conditions, cancer, metabolic conditions or conditions treatable or preventable by inhibition of a kinase or a kinase pathway, in one embodiment, the Syk, FLT-3, JAK1 and/or JAK2 and/or JAK3 and/or BTK pathway. In one embodiment an effective amount of a compound of formula (I) is an amount that inhibits a kinase in a cell, such as, for example, in vitro or in vivo. In some embodiments, the effective amount of the compound of formula (I) inhibits the kinase in a cell by 10%, 20%, 30%, 40%, 50%, 60%, 70%, 80%, 90% or 99%, compared to the activity of the kinase in an untreated cell. The effective amount of the compound of formula (I), for example in a pharmaceutical composition, may be at a level that will exercise the desired effect; for example, about 0.005 mg/kg of a subject's body weight to about 10 mg/kg of a subject's body weight in unit dosage for both oral and parenteral administration.

Use

The present compounds are suitable as pharmaceutical active ingredients for mammals, especially for humans, in the treatment of tyrosine kinase-induced diseases.

The present invention encompasses the use of the compounds of the formula I and/or physiologically acceptable salts and solvates thereof for the preparation of a medicament for the treatment or prevention of rheumatoid arthritis, systemic lupus, asthma, allergic rhinitis, ITP, multiple sclerosis, leukemia, breast cancer and maligna melanoma.

Examples of inflammatory diseases include rheumatoid arthritis, psoriasis, contact dermatitis, delayed hypersensitivity reaction and the like.

Also encompassed is the use of the compounds of the formula I and/or physiologically acceptable salts and solvates thereof for the preparation of a medicament for the treatment or prevention of a tyrosine kinase-induced disease or a tyrosine kinase-induced condition in a mammal, in which to this method a therapeutically effective amount of a compound according to the invention is administered to a sick mammal in need of such treatment. The therapeutic amount varies according to the specific disease and can be deter-mined by the person skilled in the art without undue effort.

The present invention also encompasses the use compounds of the formula I and/or physiologically acceptable salts and solvates thereof for the preparation of a medicament for the treatment or prevention of retinal vascularisation.

The expression "tyrosine kinase-induced diseases or conditions" refers to pathological conditions that depend on the activity of one or more tyrosine kinases. Tyrosine kinases either directly or indirectly participate in the signal transduction pathways of a variety of cellular activities, including proliferation, adhesion and migration and differentiation. Diseases associated with tyrosine kinase activity include proliferation of tumour cells, pathological neovascularisation that promotes the growth of solid tumours, ocular neovascularisation (diabetic retinopathy, age-induced macular degeneration and the like) and inflammation (psoriasis, rheumatoid arthritis and the like).

The present invention specifically relates to compounds of the formula I and pharmaceutically acceptable salts, solvates, tautomers and stereoisomers thereof, including mixtures thereof in all ratios, for the use for the treatment of diseases in which the inhibition, regulation and/or modulation inhibition of Syk plays a role.

The present invention specifically relates to compounds of the formula I and pharmaceutically acceptable salts, solvates, tautomers and stereoisomers thereof, including mixtures thereof in all ratios, for the use for the inhibition of Syk.

The present invention relates to a method of treating a proliferative, autoimmune, anti inflammatory or infectious disease disorder that comprises administering to a subject in need thereof a therapeutically effective amount of a compound of formula I.

Preferably, the present invention relates to a method wherein the disease is a cancer.

Particularly preferable, the present invention relates to a method wherein the disease is a cancer, wherein administration is simultaneous, sequential or in alternation with administration of at least one other active drug agent.

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic/DNA-damaging agents and combinations thereof, as used in medical oncology, such as alkylating agents (for example cis-platin, carboplatin, cyclophosphamide, nitrogen mustard, melphalan, chloroambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines, like adriamycin, bleomycin, doxorubicin, daunomycin, epirubicin, idarubicin, mitomycin-C, dactinomycin and mithramycin); antimitotic agents (for example vinca alkaloids, like vincristine, vinblastine, vindesine and vinorelbine, and taxoids, like taxol and taxotere); topoisomerase inhibitors (for example epipodophyllotoxins, like etoposide and teniposide, amsacrine, topotecan, irinotecan and camptothecin) and cell-differentiating agents (for example all-trans-retinoic acid, 13-cis-retinoic acid and fenretinide);

(ii) cytostatic agents, such as antioestrogens (for example tamoxifen, toremifene, raloxifene, droloxifene and iodoxyfene), oestrogen receptor downregulators (for example fulvestrant), antiandrogens (for example bi-calutamide, flutamide, nilutamide and cyproterone acetate), LHRH antagonists or LHRH agonists (for example goserelin, leuprorelin and buserelin), progesterones (for example megestrol acetate), aromatase inhibitors (for example as anastrozole, letrozole, vorazole and exemestane) and inhibitors of 5α-reductase, such as finasteride;

(iii) agents which inhibit cancer cell invasion (for example metallo-proteinase inhibitors, like marimastat, and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6-(3-morpholinopropoxy) quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents, such as those which inhibit the effects of vascular endothelial growth factor, (for example the anti-vascular endothelial cell growth factor antibody bevacizumab [Avastin™], compounds such as those disclosed in published international patent applications WO 97/22596, WO 97/30035, WO 97/32856 and WO 98/13354) and compounds that work by other mechanisms (for example linomide, inhibitors of integrin αvβ3 function and angiostatin);

(vi) vessel-damaging agents, such as combretastatin A4 and compounds disclosed in international patent applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-Ras antisense;

(viii) gene therapy approaches, including, for example, approaches for re-placement of aberrant genes, such as aberrant p53 or aberrant BRCA1 or BRCA2, GDEPT (gene-directed enzyme pro-drug therapy) approaches, such as those using cytosine deaminase, thymidine kinase or a bacterial nitroreductase enzyme, and approaches for increasing patient tolerance to chemotherapy or radiotherapy, such as multi-drug resistance gene therapy; and (ix) immunotherapy approaches, including, for example, ex-vivo and in-vivo approaches for increasing the immunogenicity of patient tumour cells, such as transfection with cytokines, such as interleukin 2, interleukin 4 or granulocyte-macrophage colony stimulating factor, approaches for decreasing T-cell anergy, approaches using transfected immune cells, such as cytokine-transfected dendritic cells, approaches using cytokine-transfected tumour cell lines, and approaches using anti-idiotypic antibodies.

The medicaments from Table 1 below are preferably, but not exclusively, combined with the compounds of the formula I.

TABLE 1

| | | |
|---|---|---|
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aeterna) |
| | Carboxyphthalatoplatinum | Satraplatin (Johnson Matthey) |
| | Tetraplatin | BBR-3464 (Hoffmann-La Roche) |
| | Ormiplatin | SM-11355 (Sumitomo) |
| | Iproplatin | AP-5280 (Access) |
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharrna) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | |
| | Teniposide or mitoxantrone | Quinamed (ChemGenex) |
| | | Gimatecan (Sigma-Tau) |
| | Irinotecan (CPT-11) | Diflomotecan (Beaufour-Ipsen) |
| | 7-ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | | BNP-1350 (BioNumerik) |
| | Pixantrone (Novuspharrna) | CKD-602 (Chong Kun Dang) |
| | Rebeccamycin analogue (Exelixis) | KW-2170 (Kyowa Hakko) |
| | BBR-3576 (Novuspharrna) | |
| Antitumour antibiotics | Dactinomycin (Actinomycin D) | Amonafide |
| | | Azonafide |
| | Doxorubicin (Adriamycin) | Anthrapyrazole |
| | Deoxyrubicin | Oxantrazole |
| | Valrubicin | Losoxantrone |
| | Daunorubicin (Daunomycin) | Bleomycin sulfate (Blenoxan) |
| | Epirubicin | Bleomycinic acid |
| | Therarubicin | Bleomycin A |
| | Idarubicin | Bleomycin B |
| | Rubidazon | Mitomycin C |
| | Plicamycinp | MEN-10755 (Menarini) |
| | Porfiromycin | GPX-100 (Gem Pharmaceuticals) |
| | Cyanomorpholinodoxorubicin | |
| | Mitoxantron (Novantron) | |
| Antimitotic agents | Paclitaxel | SB 408075 (GlaxoSmithKline) |
| | Docetaxel | E7010 (Abbott) |
| | Colchicine | PG-TXL (Cell Therapeutics) |
| | Vinblastine | |
| | Vincristine | |
| | Vinorelbine | IDN 5109 (Bayer) |
| | Vindesine | A 105972 (Abbott) |
| | Dolastatin 10 (NCI) | A 204197 (Abbott) |
| | Rhizoxin (Fujisawa) | LU 223651 (BASF) |
| | Mivobulin (Warner-Lambert) | D 24851 (ASTA Medica) |
| | | ER-86526 (Eisai) |
| | Cemadotin (BASF) | Combretastatin A4 (BMS) |
| | RPR 109881A (Aventis) | Isohomohalichondrin-B (PharmaMar) |
| | TXD 258 (Aventis) | |
| | Epothilone B (Novartis) | ZD 6126 (AstraZeneca) |
| | T 900607 (Tularik) | PEG-Paclitaxel (Enzon) |
| | T 138067 (Tularik) | AZ10992 (Asahi) |
| | Cryptophycin 52 (Eli Lilly) | !DN-5109 (Indena) |
| | Vinflunine (Fabre) | AVLB (Prescient NeuroPharma) |
| | Auristatin PE (Teikoku Hormone) | Azaepothilon B (BMS) |
| | BMS 247550 (BMS) | BNP-7787 (BioNumerik) |
| | BMS 184476 (BMS) | CA-4-prodrug (OXiGENE) |
| | BMS 188797 (BMS) | Dolastatin-10 (NrH) |
| | Taxoprexin (Protarga) | CA-4 (OXiGENE) |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor ™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | Ionafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | Biricodar dicitrate (Vertex) |
| | MS-209 (Schering AG) | |
| Histone acetyl transferase inhibitors | Tacedinaline (Pfizer) | Pivaloyloxymethyl butyrate (Titan) |
| | SAHA (Aton Pharma) | |
| | MS-275 (Schering AG) | Depsipeptide (Fujisawa) |
| Metalloproteinase inhibitors | Neovastat (Aeterna Laboratories) | CMT-3 (CollaGenex) |
| | | BMS-275291 (Celltech) |
| Ribonucleoside reductase inhibitors | Marimastat (British Biotech) | Tezacitabine (Aventis) |
| | | Didox (Molecules for Health) |
| | Gallium maltolate (Titan) | |
| | Triapin (Vion) | |
| TNF-alpha agonists/antagonists | Virulizin (Lorus Therapeutics) | Revimid (Celgene) |
| | CDC-394 (Celgene) | |
| Endothelin-A receptor antagonists | Atrasentan (Abbot) | YM-598 (Yamanouchi) |
| | ZD-4054 (AstraZeneca) | |
| Retinoic acid receptor agonists | Fenretinide (Johnson & Johnson) | Alitretinoin (Ligand) |
| | LGD-1550 (Ligand) | |
| Immunomodulators | Interferon | Dexosome therapy (Anosys) |
| | Oncophage (Antigenics) | |
| | GMK (Progenics) | Pentrix (Australian Cancer Technology) |
| | Adenocarcinoma vaccine (Biomira) | JSF-154 (Tragen) |
| | CTP-37 (AVI BioPharma) | Cancer vaccine (Intercell) |
| | JRX-2 (Immuno-Rx) | Norelin (Biostar) |
| | PEP-005 (Peplin Biotech) | BLP-25 (Biomira) |
| | Synchrovax vaccines (CTL Immuno) | MGV (Progenics) |
| | Melanoma vaccine (CTL Immuno) | !3-Alethin (Dovetail) |
| | | CLL-Thera (Vasogen) |
| | p21-RAS vaccine (GemVax) | |

TABLE 1-continued

| | | |
|---|---|---|
| Hormonal and antihormonal agents | Oestrogens<br>Conjugated oestrogens<br>Ethynyloestradiol chlorotrianisene<br>Idenestrol<br>Hydroxyprogesterone caproate<br>Medroxyprogesterone<br>Testosterone<br>Testosterone propionate<br>Fluoxymesterone<br>Methyltestosterone<br>Diethylstilbestrol<br>Megestrol<br>Tamoxifen<br>Toremofin<br>Dexamethasone | Prednisone<br>Methylprednisolone<br>Prednisolone<br>Aminoglutethimide<br>Leuprolide<br>Goserelin<br>Leuporelin<br>Bicalutamide<br>Flutamide<br>Octreotide<br>Nilutamide<br>Mitotan<br>P-04 (Novogen)<br>2-Methoxyoestradiol (EntreMed)<br>Arzoxifen (Eli Lilly) |
| Photodynamic agents | Talaporfin (Light Sciences)<br>Theralux (Theratechnologies)<br>Motexafin-Gadolinium (Pharmacyclics) | Pd-Bacteriopheophorbid (Yeda)<br>Lutetium-Texaphyrin (Pharmacyclics)<br>Hypericin |
| Tyrosine kinase inhibitors | Imatinib (Novartis)<br>Leflunomide(Sugen/Pharmacia)<br>ZD1839 (AstraZeneca)<br>Erlotinib (Oncogene Science)<br>Canertjnib (Pfizer)<br>Squalamine (Genaera)<br>SU5416 (Pharmacia)<br>SU6668 (Pharmacia)<br>ZD4190 (AstraZeneca)<br>ZD6474 (AstraZeneca)<br>Vatalanib (Novartis)<br>PKI166 (Novartis)<br>GW2016 (GlaxoSmithKline)<br>EKB-509 (Wyeth)<br>EKB-569 (Wyeth) | Kahalide F (PharmaMar)<br>CEP-701 (Cephalon)<br>CEP-751 (Cephalon)<br>MLN518 (Millenium)<br>PKC412 (Novartis)<br>Phenoxodiol 0<br>Trastuzumab (Genentech)<br>C225 (ImClone)<br>rhu-Mab (Genentech)<br>MDX-H210 (Medarex)<br>2C4 (Genentech)<br>MDX-447 (Medarex)<br>ABX-EGF (Abgenix)<br>IMC-1C11 (ImClone) |
| Various agents | SR-27897 (CCK-A inhibitor, Sanofi-Synthelabo)<br>Tocladesine (cyclic AMP agonist, Ribapharm)<br>Alvocidib (CDK inhibitor, Aventis)<br>CV-247 (COX-2 inhibitor, Ivy Medical)<br>P54 (COX-2 inhibitor, Phytopharm)<br>CapCell™ (CYP450 stimulant, Bavarian Nordic)<br>GCS-IOO (gal3 antagonist, GlycoGenesys)<br>G17DT immunogen (gastrin inhibitor, Aphton)<br>Efaproxiral (oxygenator, Allos Therapeutics)<br>PI-88 (heparanase inhibitor, Progen)<br>Tesmilifen (histamine antagonist, YM BioSciences)<br>Histamine (histamine H2 receptor agonist, Maxim)<br>Tiazofurin (IMPDH inhibitor, Ribapharm)<br>Cilengitide (integrin antagonist, Merck KGaA)<br>SR-31747 (IL-1 antagonist, Sanofi–Synthelabo)<br>CCI-779 (mTOR kinase inhibitor, Wyeth)<br>Exisulind (PDE-V inhibitor, Cell Pathways)<br>CP-461 (PDE-V inhibitor, Cell Pathways)<br>AG-2037 (GART inhibitor, Pfizer)<br>WX-UK1 (plasminogen activator inhibitor, Wilex)<br>PBI-1402 (PMN stimulant, ProMetic LifeSciences)<br>Bortezomib (proteasome inhibitor, Millennium)<br>SRL-172 (T-cell stimulant, SR Pharma)<br>TLK-286 (glutathione-S transferase inhibitor, Telik)<br>PT-100 (growth factor agonist, Point Therapeutics)<br>Midostaurin (PKC inhibitor, Novartis)<br>Bryostatin-1 (PKC stimulant, GPC Biotech)<br>CDA-II (apoptosis promoter, Everlife)<br>SDX-101 (apoptosis promoter, Salmedix)<br>Ceflatonin (apoptosis promoter, ChemGenex) | BCX-1777 (PNP inhibitor, BioCryst)<br>Ranpirnase (ribonuclease stimulant, Alfacell)<br>Galarubicin (RNA synthesis inhibitor, Dong-A)<br>Tirapazamine (reducing agent, SRI International)<br>N-Acetylcysteine (reducing agent, Zambon)<br>R-Flurbiprofen (NF-kappaB inhibitor, Encore)<br>3CPA (NF-kappaB inhibitor, Active Biotech)<br>Seocalcitol (vitamin D receptor agonist, Leo)<br>131-I-TM-601 (DNA antagonist, TransMolecular)<br>Eflornithin (ODC inhibitor, ILEX Oncology)<br>Minodronic acid (osteoclast inhibitor, Yamanouchi)<br>Indisulam (p53 stimulant, Eisai)<br>Aplidin (PPT inhibitor, PharmaMar)<br>Rituximab (CD20 antibody, Genentech)<br>Gemtuzumab (CD33 antibody, Wyeth Ayerst)<br>PG2 (haematopoiesis promoter, Pharmagenesis)<br>Immunol™ (triclosan mouthwash, Endo)<br>Triacetyluridine (uridine prodrug, Wellstat)<br>SN-4071 (sarcoma agent, Signature BioScience)<br>TransMID-107™ (immunotoxin, KS Biomedix)<br>PCK-3145 (apoptosis promoter, Procyon)<br>Doranidazole (apoptosis promoter, Pola)<br>CHS-828 (cytotoxic agent, Leo)<br>Trans-retinic acid (differentiator, NIH)<br>MX6 (apoptosis promoter, MAXIA)<br>Apomine (apoptosis promoter, ILEX Oncology)<br>Urocidin (apoptosis promoter, Bioniche)<br>Ro-31-7453 (apoptosis promoter, La Roche)<br>Brostallicin (apoptosis promoter, Pharmacia) |

The present invention specifically relates to compounds of the formula I and pharmaceutically acceptable salts, solvates, tautomers and stereoisomers thereof, including mixtures thereof in all ratios, for the use for the treatment of rheumatoid arthritis, systemic lupus, asthma, allergic rhinitis, ITP, multiple sclerosis, leukemia, breast cancer, maligna melanoma.

The present invention specifically relates to methods for treating or preventing an inflammatory condition, immunological condition, autoimmune condition, allergic condition, rheumatic condition, thrombotic condition, cancer, infection, neurodegenerative disease, neuroinflammatory disease, cardiovascular disease or metabolic condition, comprising administering to a subject in need thereof an effective amount of a compound of formula I or a pharmaceutically acceptable salt, tautomer, stereoisomer or solvate thereof.

In another aspect provided herein are methods of inhibiting a kinase in a cell expressing said kinase, comprising contacting said cell with an effective amount of a compound of formula I or a pharmaceutically acceptable salt, tautomer, stereoisomer or solvate thereof. In one embodiment the kinase is Syk, FLT3, JAK1 or JAK2 or JAK3 or BTK, or mutants or isoforms thereof, or combinations of two or more thereof.

Representative immunological conditions that compounds of formula I are useful for treating or preventing include, but are not limited to, Behcet's syndrome, non-allergy mast cell diseases (e.g., mastocytosis and treatment of anaphylaxis), ankylosing spondylitis, osteoarthritis, rheumatoid arthritis (RA), multiple sclerosis, lupus, inflammatory bowel disease, ulcerative colitis, Crohn's disease, myasthenia gravis, Grave's disease, transplant rejection, humoral transplant rejection, non-humoral transplant rejection, cellular transplant rejection, immune thrombocytopenic purpura (ITP), idiopathic thrombocytopenic purpura, diabetes, immunological response to bacterial, parasitic, helminth infestation or viral infection, eczema, dermatitis, graft versus host disease, Goodpasture's disease, hemolytic disease of the newborn, autoimmune hemolytic anemia, anti-phospholipid syndrome, ANCA-associated vasculitis, Churg-Strauss syndrome, Wegeners granulomatosus, pemphigus vulgaris, serum sickness, mixed cryoglobulinemia, peripheral neuropathy associated with IgM antibody, microscopic polyangiitis, Hashimoto's thyroiditis, Sjogrens syndrome, fibrosing conditions (such as those dependent on the innate or adaptive immune systems or local mesenchyma cells) or primary biliary cirrhosis.

Representative autoimmune conditions that compounds of formula I are useful for treating or preventing include, but are not limited to, autoimmune hemolytic anemia (A1HA), Behcet's syndrome, Crohn's disease, type I diabetes, Goodpasture's disease, Grave's disease, Hashimoto's thyroiditis, idiopathic thrombocytopenic purpura, lupus, multiple sclerosis, amyotrophic lateral sclerosis, myasthenia gravis, pemphigus vulgaris, primary biliary cirrhosis, rheumatoid arthritis, scleroderma, Sjogren's syndrome, ulcerative colitis, or Wegeners granulomatosus.

Representative allergic conditions that compounds of formula I are useful for treating or preventing include, but are not limited to, anaphylaxis, hay fever, allergic conjunctivitis, allergic rhinitis, allergic asthma, atopic dermatitis, eczema, urticaria, mucosal disorders, tissue disorders and certain gastrointestinal disorders.

Representative rheumatic conditions that compounds of formula I are useful for treating or preventing include, but are not limited to, rheumatoid arthritis, gout, ankylosing spondylitis, or osteoarthritis.

Representative inflammatory conditions that compounds of formula I are useful for treating or preventing include, but are not limited to, non-ANCA (anti-neutrophil cytoplasmic autoantibody) vasculitis (e.g., wherein Syk function is associated with neutrophil adhesion, diapedesis and/or activation), psoriasis, asthma, allergic rhinitis, allergic conjunctivitis, chronic urticaria, hives, anaphylaxis, bronchitis, chronic obstructive pulmonary disease, cystic fibrosis, inflammatory bowel disease, irritable bowel syndrome, gout, Crohn's disease, mucous colitis, ulcerative colitis, allergy to intestinal antigens (such as gluten enteropathy), diabetes (e.g., Type I diabetes and Type II diabetes) and obesity. In some embodiments, the inflammatory condition is a dermatologic condition, such as, for example, psoriasis, urticaria, hives, eczema, scleroderma, or dermatitis. In other embodiments, the inflammatory condition is an inflammatory pulmonary condition, such as, for example, asthma, bronchitis, chronic obstructive pulmonary disease (COPD), or adult/acute respiratory distress syndrome (ARDS). In other embodiments, the inflammatory condition is a gastrointestinal condition, such as, for example, inflammatory bowel disease, ulcerative colitis, Crohn's disease, idiopathic inflammatory bowel disease, irritable bowel syndrome, or spastic colon.

Representative infections that compounds of formula I are useful for treating or preventing include, but are not limited to, bacterial, parasitic, prion, viral infections or helminth infestation.

Representative cancers that compounds of formula I are useful for treating or preventing include, but are not limited to, cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, brain, central nervous system, solid tumors and blood-borne tumors.

Representative cardiovascular diseases that compounds of formula I are useful for treating or preventing include, but are not limited to, restenosis, atherosclerosis and its consequences such as stroke, myocardial infarction, ischemic damage to the heart, lung, gut, kidney, liver, pancreas, spleen or brain.

Representative metabolic conditions that compounds of formula I are useful for treating or preventing include, but are not limited to, obesity and diabetes (e.g., Type I and II diabetes). In a particular embodiment, provided herein are methods for the treatment or prevention of insulin resistance. In certain embodiments, provided herein are methods for the treatment or prevention of insulin resistance that leads to diabetes (e.g., Type II diabetes). In another embodiment, provided herein are methods for the treatment or prevention of syndrome X or metabolic syndrome. In another embodiment, provided herein are methods for the treatment or prevention of Type II diabetes, Type I diabetes, slow-onset Type I diabetes, diabetes insipidus (e.g., neurogenic diabetes insipidus, nephrogenic diabetes insipidus, dipsogenic diabetes insipidus, or gestagenic diabetes insipidus), diabetes mellitus, gestational diabetes mellitus, polycystic ovarian syndrome, maturity-onset diabetes, juvenile diabetes, insulin-dependant diabetes, non-insulin dependant diabetes, malnutrition-related diabetes, ketosis-prone diabetes, pre-diabetes (e.g., impaired glucose metabolism), cystic fibrosis related diabetes, hemochromatosis and ketosis-resistant diabetes.

Representative neurodegenerative and neuroinflammatory diseases that compounds of formula I are useful for treating or preventing include, but are not limited to, Huntington's disease, Alzheimer's disease, viral (e.g., HIV) or bacterial-associated encephalitis and damage.

In another embodiment, provided herein are methods for the treatment or prevention of fibrotic diseases and disorders. In a particular embodiment, provided herein are methods for the treatment or prevention of idiopathic pulmonary fibrosis, myelofibrosis, hepatic fibrosis, steatofibrosis and steatohepatitis.

In another embodiment, provided herein are methods for the treatment or prevention of diseases associated with thrombotic events such as but not limited to atherosclerosis, myocardial infarction and ischemic stroke.

The present invention specifically relates to compounds of the formula I and pharmaceutically acceptable salts, solvates, tautomers and stereoisomers thereof, including mixtures thereof in all ratios, for the use for the treatment and/or prevention of inflammatory conditions, immunological conditions, autoimmune conditions, allergic conditions, rheumatic conditions, thrombotic conditions, cancer, infections, neurodegenerative diseases, neuroinflammatory diseases, cardiovascular diseases, and metabolic conditions, the methods comprising administering to a subject in need thereof an effective amount of a compound of claim 1.

Moreover, the present invention specifically relates to compounds for the use for the treatment and/or prevention of cancer, where the cancer to be treated is a solid tumour or a tumour of the blood and immune system.

Moreover, the present invention specifically relates to compounds, for the use for the treatment and/or prevention of cancer, where the where the tumour originates from the group of acute myeloid leukaemia, chronic myeloid leukaemia, acute lymphatic leukaemia and/or chronic lymphatic leukaemia.

Moreover, the present invention specifically relates to compounds, for the use for the treatment and/or prevention of cancer, where the solid tumour originates from the group of tumours of the epithelium, the bladder, the stomach, the kidneys, of head and neck, the esophagus, the cervix, the thyroid, the intestine, the liver, the brain, the prostate, the uro-genital tract, the lymphatic system, the stomach, the larynx, the bones, including chondosarcoma and Ewing sarcoma, germ cells, including embryonal tissue tumours, and/or the lung, from the group of monocytic leukaemia, lung adenocarcinoma, small-cell lung carcinomas, pancreatic cancer, glioblastomas, neurofibroma, angiosarcoma, breast carcinoma and/or maligna melanoma.

Moreover, the present invention specifically relates to for the use for the treatment and/or prevention of diseases selected from the group rheumatoid arthritis, systemic lupus, asthma, multiple sclerosis, osteoarthritis, ischemic injury, giant cell arteritis, inflammatory bowel disease, diabetes, cystic fibrosis, psoriasis, Sjogrens syndrome and transplant organ rejection.

Moreover, the present invention specifically relates to compounds for the use for the treatment and/or prevention of diseases selected from the group Alzheimer's disease, Down's syndrome, hereditary cerebral hemorrhage with amyloidosis-Dutch Type, cerebral amyloid angiopathy, Creutzfeldt-Jakob disease, frontotemporal dementias, Huntington's disease, Parkinson's disease.

Moreover, the present invention specifically relates to compounds for the use for the treatment and/or prevention of diseases selected from the group *leishmania*, mycobacteria, including *M. leprae, M. tuberculosis* and/or *M. avium, leishmania, plasmodium*, human immunodeficiency virus, Epstein Barr virus, Herpes simplex virus, hepatitis C virus.

The following abbreviations refer respectively to the definitions below: aq (aqueous), h (hour), g (gram), L (liter), mg (milligram), MHz (Megahertz), min. (minute), mm (millimeter), mmol (millimole), mM (millimolar), m.p. (melting point), eq (equivalent), mL (milliliter), L (microliter), ACN (acetonitrile), AcOH (acetic acid), $CDCl_3$ (deuterated chloroform), $CD_3OD$ (deuterated methanol), $CH_3CN$ (acetonitrile), c-hex (cyclohexane), DCC (dicyclohexyl carbodiimide), DCM (dichloromethane), DIC (diisopropyl carbodiimide), DIEA (diisopropylethyl-amine), DMF (dimethylformamide), DMSO (dimethylsulfoxide), DMSO-$d_6$ (deuterated dimethylsulfoxide), EDC (1-(3-dimethyl-aminopropyl)-3-ethylcarbodiimide), ESI (Electro-spray ionization), EtOAc (ethyl acetate), $Et_2O$ (diethyl ether), EtOH (ethanol), HATU (dimethylamino-([1,2,3]triazolo[4,5-b]pyridin-3-yloxy)-methylene]-dimethyl-ammonium hexafluorophosphate), HPLC (High Performance Liquid Chromatography), i-PrOH (2-propanol), $K_2CO_3$ (potassium carbonate), LC (Liquid Chromatography), MeOH (methanol), $MgSO_4$ (magnesium sulfate), MS (mass spectrometry), MTBE (Methyl tert-butyl ether), $NaHCO_3$ (sodium bicarbonate), $NaBH_4$ (sodium borohydride), NMM (N-methyl morpholine), NMR (Nuclear Magnetic Resonance), PyBOP (benzotriazole-1-yloxy-tris-pyrrolidino-phosphonium hexafluorophosphate), RT (room temperature), Rt (retention time), SPE (solid phase extraction), TBTU (2-(1-H-benzotriazole-1-yl)-1,1,3,3-tetramethyluromium tetrafluoro borate), TEA (triethylamine), TFA (trifluoroacetic acid), THF (tetrahydrofuran), TLC (Thin Layer Chromatography), UV (Ultraviolet).

Description of the In Vitro Assays
SYK Flash Plate Assay

The kinase assay is performed either as 384-well Flashplate assay (for e.g. Topcount measurement) or as 384-well Image-Flashplate assay (for LEADseeker measurement).

2.5 nM SYK, 400 nM Biotin-Aha-Aha-KEDPDYEWP-SAKK and 10 μM ATP (spiked with 0.3 μCi 33P-ATP/well) are incubated in a total volume of 50 μl (60 mM Hepes, 10 mM $MgCl_2$, 1.2 mM Dithiothreitol, 0.02% Brij35, 0.1% BSA, pH 7.5) with or without test compound for 1 hours at 30° C. The reaction is stopped with 25 μl 200 mM EDTA. After 30 Min at 30° C. the liquid is removed and each well washed thrice with 100 μl 0.9% sodium chloride solution. Non-specific reaction is determined in presence of 0.1 μM Staurosporine. Radioactivity is measured with Topcount (when using Flashplates) or with LEADseeker (when using Image-Flashplates) respectively. Results (e.g. IC50-values) are calculated with program tools provided by the IT-department (e.g. Symyx Assay Explorer, Genedata Screener).

In vivo Assays
CIA

For induction of collagen-induced arthritis (CIA) male DBA/1 mice are injected with 500 μl pristane i.p. on day −21. On day 0 mice are immunized with 100 μg chicken collagen type II (CII) in Complete Freund's Adjuvant (CFA) intradermally, distributed over pinnae and one site on the back on day 0. On day 21, mice will receive an i.p. booster immunization (100 μg) with soluble CII in PBS. Dosing of Syk inhibitor will be prophylactic: starting day 0 and continued until day 10 and before boost starting on day 20 and continued until day 30. Compounds will be administered orally twice a day at doses of 3, 10 and 30 mg/kg.

Body weight and clinical score will be recorded on a daily basis. Arthritis severity is graded using a clinical scoring system based on the assessment of inflammation in individual paws. The scale for this clinical score ranges from 0-4 for each individual paw.

GIA

For induction of Glucose-6-phosphate isomerase-induced arthritis (GIA) female DBA/1 mice are immunized with 100 μg G6PI in Complete Freund's Adjuvant (CFA) intradermally, distributed over pinnae and one site on the back on day 0. Dosing of Syk inhibitor will be prophylactic starting day 0 and continued until day 14. Compounds will be administered orally twice a day at doses of 3, 10 and 30 mg/kg.

Body weight and clinical score will be recorded on a daily basis. Arthritis severity is graded using a clinical scoring system based on the assessment of inflammation in individual paws. The scale for this clinical score ranges from 0-4 for each individual paw.

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the residue is purified by chromatography on silica gel and/or by crystallisation. Rf values on silica gel; eluent: ethyl acetate/methanol 9:1.

Mass spectrometry (MS): EI (electron impact ionisation) M$^+$
FAB (fast atom bombardment) (M+H)$^+$
ESI (electrospray ionisation) (M+H)$^+$
APCI-MS (atmospheric pressure chemical ionisation-mass spectrometry) (M+H)$^+$.

Mass spectrometry (MS): EI (electron impact ionisation) M$^+$
FAB (fast atom bombardment) (M+H)$^+$
ESI (electrospray ionisation) (M+H)$^+$
m.p.=melting point
LCMS Method:
Column: ZORBAX SB-C8 30*4.6 mm, 3.5 um
Mobile Phase A: Water+0.03% TFA
Mobile Phase B: ACN+0.05% TFA
Gradient: 5-95% B in 2.5 minutes
Flow: 2.0 mL/min
Wavelength: UV1:220 nm, UV2:254 nm
Mass Scan: 100-900 Da
GCN2: Assay Principle & Conditions This assay can quantificate the activity of the serin kinase GCN2 (general control non-derepressible-2).

This kinase is involved in the stress metabolism of cells. It is activated upon starvation (amino acid depletion). Its natural substrate is eIF2a (eukaryotic initiation factor 2 alpha subunit), a translation factor, which gets activated (phosphorylated) by GCN2 in case of an amino acid bottleneck in the cells. This in turn leads to a halt of the protein synthesis. Inhibition of GCN2 results in stopping this mechanism: The cell can not stop protein production upon "starvation" stress.

The assay is run in two steps: the enzymatic reaction and the detection step. In the first step GCN2 is incubated with 10 μM ATP and 80 nM of the GFP-labelled substrate eIF2alpha at room temperature.

The enzymatic reaction is stopped by addition of EDTA. The amount of phosphorylated eIF2alpha is determined by TR-FRET (Lanthascreen): A complex is formed consisting of antibody and GFP labelled phospho-eIF2a, which allows a FRET upon exitation at 340 nm.

The GCN2-activity is directly proportional to the ratio of fluorescence units at the emission wavelength 520 nm (phosphopeptide-sensitive wavelength=emission of GFP) to the units at 495 nm (reference wavelength=emission of Terbium-chelate).

Final Concentrations in the Enzymatic Reaction

| | |
|---|---|
| Hepes, pH 7.0 | 50 mM |
| $MgCl_2$ | 10 mM |
| $MnCl_2$ | 5 mM |
| BSA | 0.1% |
| DMSO | 1% |
| ATP | 10 uM |
| DTT | 2 mM |
| GFP-eIF2a | 80 nM (substrate) |
| GCN2 | 30 nM (enzyme) |

Assay Procedure

| | |
|---|---|
| 4 uL | enzyme solution (in assay buffer) |
| 1.5 uL | compound (in cmpd dilution buffer/6.3% DMSO) |
| Incubation | 20 min at RT |
| 4 uL | substrate/ATP mix (in assay buffer) |
| Incubation | 90 min at RT |
| 10 uL | stop/detection mix (in antibody dilution buffer) |
| Incubation | 60 min at RT |
| Readout | Lanthascreen 340/495/520 |

Standard Description of Analytical Equipment $^1$H NMR was recorded on a Joel 400 MHz spectrometer, using residual signal of deuterated solvent as internal reference. Chemical shifts (δ) are reported in ppm relative to the residual solvent signal (δ=2.49 ppm for $^1$H NMR in DMSO-$d_6$). $^1$H NMR data are reported as follows: chemical shift (multiplicity, coupling constants, and number of hydrogens). Multiplicity is abbreviated as follows: s (singlet), d (doublet), t (triplet), q (quartet), m (multiplet), br (broad).

LCMS method:

Column: Xbridge C8, 4.6×50 mm 5 μm

Mobile Phase A: Water+0.1% TFA

Mobile Phase B: ACN+0.1% TFA

Gradient: 5-95% B in 3.5 minutes

Flow: 0.8 mL/min

Wavelength: 254 nm

Mass Scan: 100-900 Da

EXAMPLE 1

The preparation of

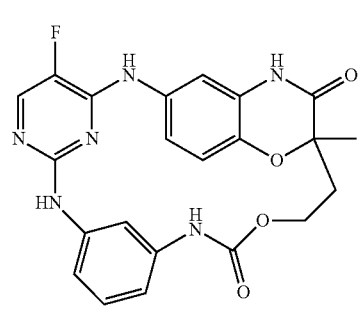

"6"

is carried out analogously to the following scheme:

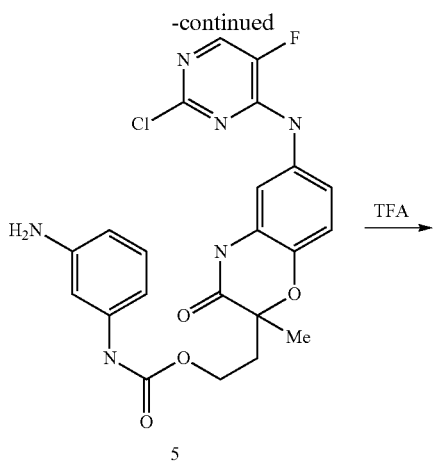

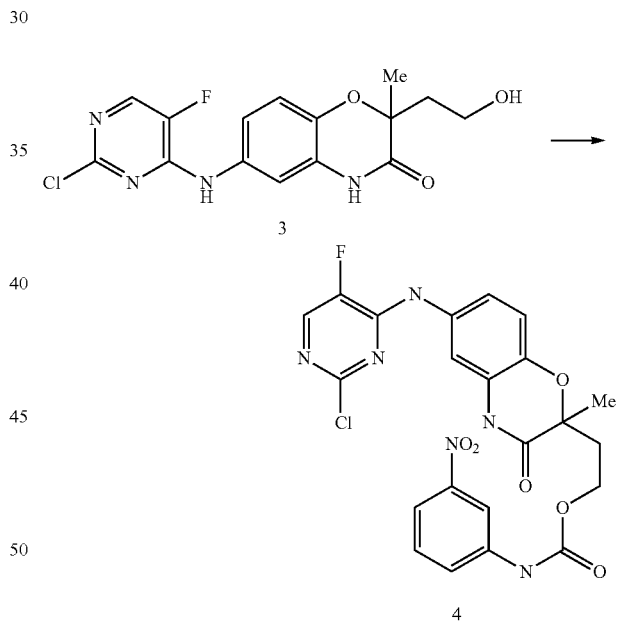

1.1 Preparation of 2-(2-hydroxyethyl)-2-methyl-6-nitro-2H-1,4-benzoxazin-3(4H)-one (1)

To a solution of 2-amino-4-nitrophenol (1.00 g; 6.49 mmol; 1.00 eq.) in benzene (5.00 ml) at 0° C. (ice bath) is added trimethylaluminum (3.57 ml; 7.14 mmol; 1.10 eq.; 2.00 M in hexanes). The reaction mixture is stirred for 45 minutes, then a solution of 3-bromo-3-methyldihydrofuran-2(3H)-one (0.73 ml; 6.49 mmol; 1.00 eq.) in dichloromethane (5.00 ml) is added and the resultant solution allowed to warm to room temperature. Upon warming the reaction flask is heated to 65° C. for 15 hours then cooled again to 0° C. via ice bath.

To the chilled flask, is added 1N HCl (aq) slowly to quench the reaction, which is stirred for an additional 30 minutes. The reaction mixture is extracted with ethyl acetate. The combined organic fractions are dried over magnesium sulfate, filtered and concentrated. The residue is then dissolved in ACN then heated to reflux overnight with potassium carbonate (0.37 ml; 6.49 mmol; 1.00 eq.), which, upon filtering through a celite plug and purified through flash chromatography yielded 2-(2-hydroxyethyl)-2-methyl-6-nitro-2H-1,4-benzoxazin-3(4H)-one (0.98 g, 60.1%). Jeol $^1$H NMR (400 MHz, DMSO-$d_6$) δ 7.95, 7.86, 7.86, 7.84, 7.84, 7.73, 7.73, 7.16, 7.14, 3.17, 3.16, 2.89, 2.73, 1.47. LCMS: rt 2.35; m/z 252.96.

1.2 Preparation of 6-amino-2-(2-hydroxyethyl)-2-methyl-2H-1,4-benzoxazin-3(4H)-one (2)

A flask containing 2-(2-hydroxyethyl)-2-methyl-6-nitro-2H-1,4-benzoxazin-3(4H)-one (983.30 mg; 3.90 mmol; 1.00 eq.) dissolved in methanol (10.00 ml) is passed through the H-Cube using 10% Pd/C cartridge, at 1 mL per minute, in full $H_2$ mode at 30 C. The product is afforded quantitatively upon concentration of the eluent and used directly in further reactions; LCMS: rt 0.24 min; m/z 223.06.

1.3 Preparation of 6-[(2-chloro-5-fluoropyrimidin-4-yl)amino]-2-(2-hydroxyethyl)-2-methyl-2H-1,4-benzoxazin-3(4H)-one (3)

Into a clean round bottom flask equipped with a stirbar 2,4-dichloro-5-fluoropyrimidine (500.00 mg; 2.99 mmol; 1.00 eq.) and 6-amino-2-(2-hydroxyethyl)-2-methyl-2H-1,4-benzoxazin-3(4H)-one(2) (0.73 g; 3.29 mmol; 1.10 eq.) are dissolved in tetrahydronfuran (30 mL). To the stirred solution is added triethylamine (0.46 ml; 3.29 mmol; 1.10 eq.). The reaction is stirred at ambient temperature for 16 hours. Upon completion, the reaction mixture is concentrated to a residue, dissolved in minimal dichloromethane and purified with flash chromatography using a gradient of 0-10% methanol in dichloromethane to give 6-[(2-chloro-5-fluoropyrimidin-4-yl)amino]-2-(2-hydroxyethyl)-2-methyl-2H-1,4-benzoxazin-3(4H)-one(3) (243.8 mg; 0.69 mmol; 23.1%); LCMS: rt 2.82 min; m/z 353.09.

1.4 Preparation of 2-{6-[(2-chloro-5-fluoropyrimidin-4-yl)amino]-2-methyl-3-oxo-3,4-dihydro-2H-1,4-benzoxazin-2-yl}ethyl (3-nitrophenyl)carbamate (4)

Into a round bottom flask equipped with a stir bar 3-nitroaniline (78.31 mg; 0.57 mmol; 2.00 eq.) is dissolved in THF. To this mixture N,N-diethylethanamine (0.08 ml; 0.57 mmol; 2.00 eq.) is added followed by 4-nitrophenyl chloride-carbonate (114.28 mg; 0.57 mmol; 2.00 eq.) via syringe. The reaction mixture is allowed to stir for 30 minutes. To the reaction flask 6-[(2-chloro-5-fluoropyrimidin-4-yl)amino]-2-(2-hydroxyethyl)-2-methyl-2H-1,4-benzoxazin-3(4H)-one(3) (100.00 mg; 0.28 mmol; 1.00 eq.) is added in 1 mL of dimethylformamide. The reaction is stirred for 16 hours at ambient temperature. The reaction crude is diluted with ethyl acetate (200 mL) and extracted with brine solution. The organic layer is dried over magnesium sulfate, filtered and concentrated to a crude viscous oil which is purified with flash chromatography using a gradient of 0-100% ethyl acetate in hexanes followed by a gradient of 0-25% methanol in ethyl acetate to give 2-{6-[(2-chloro-5-fluoropyrimidin-4-yl)amino]-2-methyl-3-oxo-3,4-dihydro-2H-1,4-benzoxazin-2-yl}ethyl (3-nitrophenyl)carbamate (4) (35.9 mg; 0.07 mmol; 24.5%) as an off white solid; Jeol ¹H NMR (400 MHz, DMSO-d₆) δ 8.53, 8.53, 7.84, 7.84, 7.83, 7.83, 7.82, 7.82, 7.81, 7.73, 7.73, 7.72, 7.71, 7.71, 7.70, 7.54, 7.54, 7.52, 7.52, 7.50, 7.50, 4.22, 4.18, 3.15, 1.94, 1.42, 1.16, 1.15, 1.13. LCMS: rt 3.57 min; m/z 517.15.

1.5 Preparation of 2-{6-[(2-chloro-5-fluoropyrimidin-4-yl)amino]-2-methyl-3-oxo-3,4-dihydro-2H-1,4-benzoxazin-2-yl}ethyl (3-aminophenyl)carbamate (5)

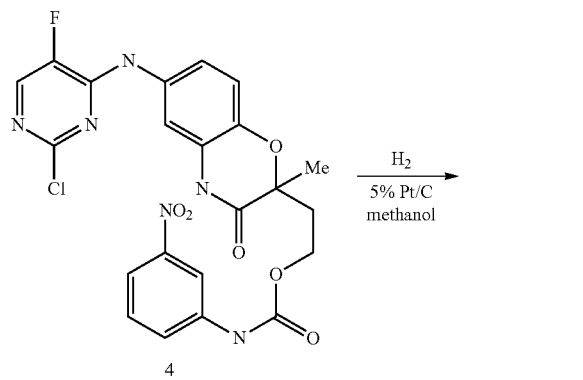

2-6[(2-chloro-5-fluoropyrimidin-4-yl)amino]-2-methyl-3-oxo-3,4-dihydro-2H-1,4-benzoxazin-2-ylethyl (3-nitrophenyl)carbamate(4) (144.70 mg; 0.28 mmol; 1.00 eq.) is dissolved in methanol (35.00 ml) then passed through a H-Cube reactor equipped with 5% Pt/C cartridge at 1 mL/min at 30° C. in full H2 mode. The desired product is purified by Prep HPLC using a gradient of 10-50% acetonitrile in water with 0.1% trifluoroacetic acid modifier to give a white powder, 2-{6[(2-chloro-5-fluoropyrimidin-4-yl)amino]-2-methyl-3-oxo-3,4-dihydro-2H-1,4-benzoxazin-2-yl}ethyl (3-aminophenyl)carbamate (5) (15.2 mg; 0.3 mmol; 11.2%); LCMS: rt 3.70 min; m/z 518.12.

1.6 Cyclization of 2-{6[(2-chloro-5-fluoropyrimidin-4-yl)amino]-2-methyl-3-oxo-3,4-dihydro-2H-1,4-benzoxazin-2-yl}ethyl (3-aminophenyl)carbamate (5) to give macrocycle (6)

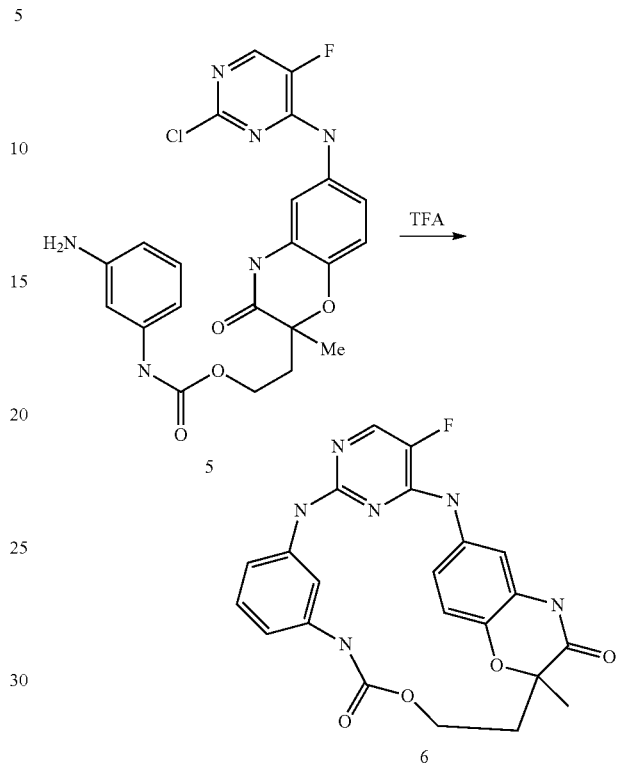

Into a 2-necked flask, equipped with condenser and stirbar was added acetonitrile (45 mL), dimethylformamide (5 mL) and trifluoroacetic acid (3.56 mg; 0.03 mmol; 1.00 eq.). The reaction vessel was brought to reflux. To the reaction vessel was added 2-(2-{([2-(3-aminophenyl)ethyl]amino}ethyl)-6-[(2-chloro-5-fluoro-pyrimidin-4-yl)amino]-2-methyl-2H-1,4-benzoxazin-3(4H)-one(6) (59.9 mg; 0.13 mmol; 1.00 eq.) in acetonitrile (5 mL) dropwise via syringe pump. The reaction was allowed to reflux for 16 hours, then the crude concentrated and purified via Prep HPLC using a 10-40% acetonitrile in water with 0.1% trifluoroacetic acid modifier to give the desired product, 6 (9.6 mg; 0.02 mmol; 68.3%). Jeol ¹H NMR (400 MHz, METHANOL-D₃) δ 9.07, 8.37, 8.02, 8.01, 7.23, 7.23, 7.21, 7.19, 7.06, 7.05, 7.04, 6.92, 6.90, 6.78, 6.77, 6.75, 6.74, 6.73, 4.43, 4.40, 4.38, 4.19, 4.18, 4.17, 4.16, 4.15, 4.15, 2.99, 2.85, 2.65, 1.67;

LCMS: rt 2.35 min; m/z 451.20.

EXAMPLE 2

Preparation of "9"

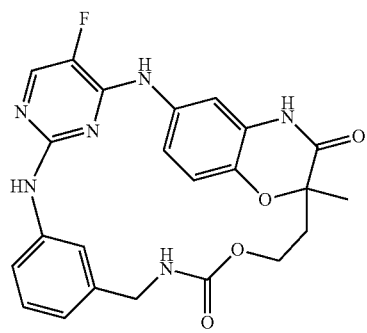

2.1 Preparation of 2-{6-[(2-chloro-5-fluoropyrimidin-4-yl)amino]-2-methyl-3-oxo-3,4-dihydro-2H-1,4-benzoxazin-2-yl}ethyl (3-nitrobenzyl)carbamate (7)

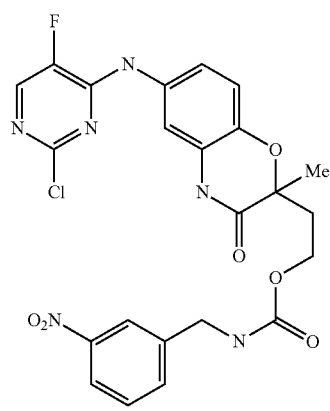

The preparation of (7) is carried out analogously to the procedure described in preparation of (4); yield: 92.3 mg (0.17 mmol; 61.3%); LCMS: rt 2.98 min; m/z 530.90.

2.2 Preparation of 2-{6-[(2-chloro-5-fluoropyrimidin-4-yl)amino]-2-methyl-3-oxo-3,4-dihydro-2H-1,4-benzoxazin-2-yl}ethyl (3-aminobenzyl)carbamate (8)

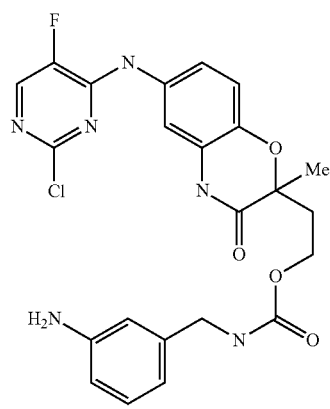

The preparation of (8) starting from (7) is carried out analogously to the procedure described in preparation of (5); yield: 74.2 mg (0.15 mmol; 85.2%); LCMS: rt 2.72 min; m/z 500.90.

2.3 The preparation of (9) starting from (8) is carried out analogously to the procedure described in preparation of (6); yield: 3.1 mg (0.01 mmol; 4.5%); Jeol $^1$H NMR (400 MHz, methanol-$d_3$) δ 8.04, 8.03, 7.30, 7.29, 7.25, 7.19, 7.16, 7.14, 7.03, 6.99, 6.93, 4.40, 4.40, 4.25, 4.21, 4.19, 2.65, 1.62, 1.54, 1.28; LCMS: rt 2.57 min; m/z 465.18.

EXAMPLE 3

Preparation of

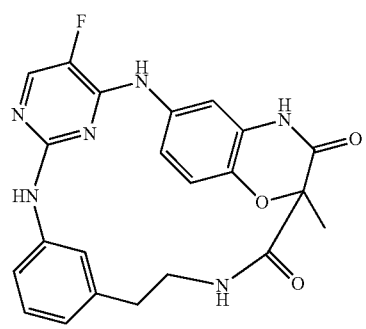

"12"

3.1 Preparation of 6-[(2-chloro-5-fluoropyrimidin-4-yl)amino]-2-methyl-N-[2-(3-nitro-phenyl)ethyl]-3-oxo-3,4-dihydro-2H-1,4-benzoxazine-2-carboxamide (10)

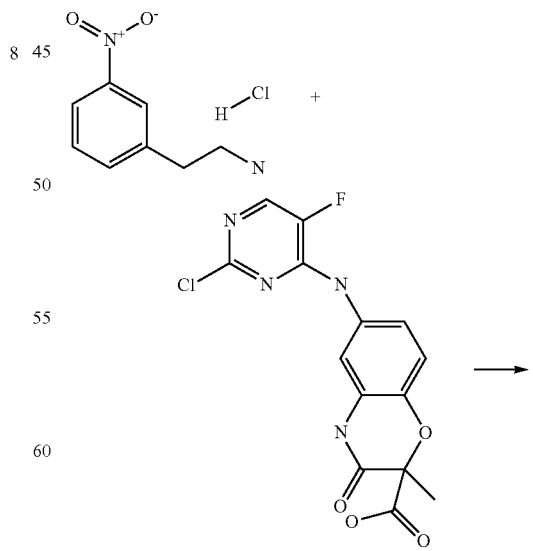

SYN5052A

-continued

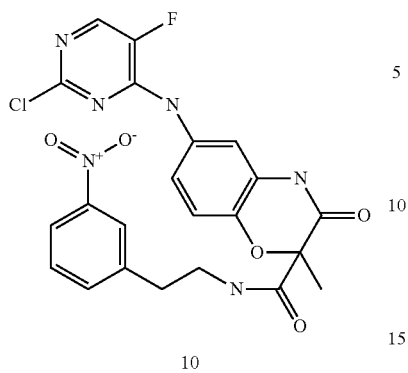

10

2-(3-nitrophenyl)ethanamine hydrochloride (100.00 mg; 0.49 mmol; 1.00 eq.), 6-[(2-chloro-5-fluoropyrimidin-4-yl)amino]-2-methyl-3-oxo-3,4-dihydro-2H-1,4-benzoxazine-2-carboxylic acid (SYN5052A) (174.06 mg; 0.49 mmol; 1.00 eq.), o-(7-azabenzotriazol-1-yl)-n,n,n',n'-tetra-methyluronium hexafluorophosphate (375.28 mg; 0.99 mmol; 2.00 eq.) and N-ethyl-N-isopropylpropan-2-amine (0.32 ml; 1.97 mmol; 4.00 eq.) are placed into a scintillation vial equipped with a stir bar. The mixture is taken up in DMF (3.00 ml). The reaction mixture is stirred for 16 hours. Upon completion, the reaction mixture is diluted with ethyl acetate (100 mL) and extracted with brine solution. The organic layer is then dried over magnesium sulfate, filtered, concentrated and purified via Prep HPLC using a gradient of 10-50% acetonitrile in water with 0.1% trifluoroacetic acid modifier to give 6-[(2-chloro-5-fluoropyrimidin-4-yl)amino]-2-methyl-N-[2-(3-nitrophenyl)ethyl]-3-oxo-3,4-dihydro-2H-1,4-benzoxazine-2-carboxamide (10) (226.4 mg; 0.45 mmol; 91.6%);

Jeol $^1$H NMR (400 MHz, methanol-$d_3$) δ 8.11, 8.10, 7.99, 7.98, 7.44, 7.42, 7.37, 7.35, 7.34, 7.17, 7.17, 7.15, 7.14, 6.98, 6.96, 4.10, 4.08, 3.57, 3.56, 3.12, 2.85, 2.84, 2.82, 2.80, 2.03, 2.00, 1.68, 1.36, 1.34, 1.25, 1.23, 1.21;

LCMS: rt 3.19 min; m/z 501.12.

3.2 Preparation of N-[2-(3-aminophenyl)ethyl]-6-[(2-chloro-5-fluoro-pyrimidin-4-yl)amino]-2-methyl-3-oxo-3,4-dihydro-2H-1,4-benzoxazine-2-carboxamide (11) from (10)

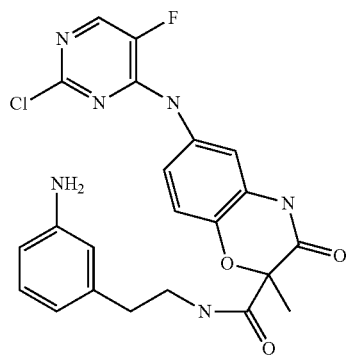

11

The preparation of (11) is carried out analogously to the procedure described in preparation of (5); yield: 23.1 mg (0.05 mmol; 10.9%); Jeol $^1$H NMR (400 MHz, methanol-$d_3$) δ 8.35, 8.11, 8.10, 7.40, 7.39, 7.34, 7.32, 7.23, 7.22, 7.20, 7.20, 7.11, 7.08, 7.06, 6.99, 6.97, 3.43, 3.39, 3.38, 3.36, 2.74, 2.72, 2.70, 2.65, 1.66; LCMS: rt 2.03 min; m/z 471.18.

3.3 The preparation of (12) starting from (11) is carried out analogously to the procedure described in preparation of (6); yield: 2.1 mg (0.004 mmol; 12.2%);

$^1$H NMR (Jeol 400 MHz, methanol-$d_3$) δ 8.27, 8.26, 8.24, 8.06, 8.05, 7.43, 7.41, 7.37, 7.34, 7.34, 7.23, 7.21, 7.19, 7.16, 7.16, 7.14, 7.14, 6.98, 6.96, 6.86, 6.84, 3.44, 3.44, 3.43, 3.42, 3.41, 3.39, 3.37, 3.36, 3.34, 3.33, 3.31, 2.67, 2.65, 2.64, 1.66; LCMS: rt 0.65 min; m/z 435.18.

EXAMPLE 4

Preparation of "15"

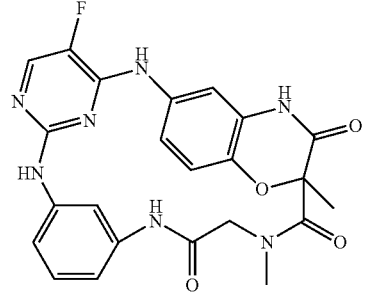

4.1 Preparation of 6-[(2-chloro-5-fluoropyrimidin-4-yl)amino]-N,2-dimethyl-N-{2-[(3-nitrophenyl)amino]-2-oxoethyl}-3-oxo-3,4-dihydro-2H-1,4-benzoxazine-2-carboxamide (13)

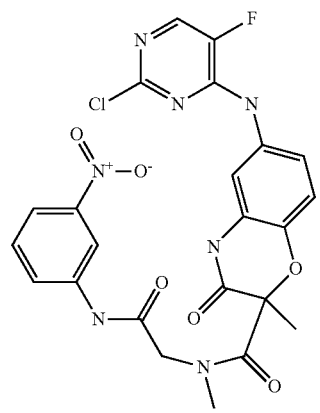

13

The preparation of (13) is carried out analogously to the procedure described in preparation of (11); yield: 341.5 mg (0.63 mmol; 71.9%); LCMS: rt 3.37 min; m/z 543.97.

4.2 Preparation of N-{2-[(3-aminophenyl)amino]-2-oxoethyl}-6-[(2-chloro-5-fluoro-pyrimidin-4-yl)amino]-N,2-dimethyl-3-oxo-3,4-dihydro-2H-1,4-benzoxazine-2-carboxamide (14)

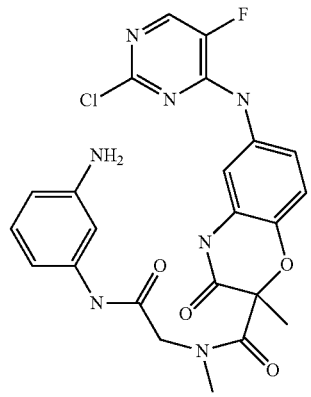

14

The preparation of (14) is carried out analogously to the procedure described in preparation of (5); yield: 42 mg (0.08 mmol; 44.6%);
$^1$H NMR (Jeol 400 MHz, methanol-$d_3$) δ 8.07, 8.06, 7.99, 7.44, 7.44, 7.40, 7.39, 7.23, 7.23, 7.21, 7.20, 7.06, 7.04, 7.04, 7.03, 7.02, 7.02, 7.01, 4.10, 4.08, 3.33, 2.98, 1.72;
LCMS: rt 2.54 min; m/z 513.81.

4.3 Preparation of (15) starting from (14) is carried out analogously to the procedure described in preparation of (6); yield: 9.5 mg (0.02 mmol; 33.9%); Jeol $^1$H NMR (400 MHz, methanol-$d_3$) δ 9.38, 9.29, 8.40, 8.05, 8.04, 7.67, 7.37, 7.37, 7.25, 7.23, 7.17, 6.91, 6.77, 6.63, 6.61, 5.55, 5.51, 5.47, 4.38, 4.34, 4.02, 3.98, 3.94, 3.51, 2.88, 2.85, 1.93, 1.86, 1.67;

LCMS: rt 2.44 min; m/z 478.19.

EXAMPLE 5

Preparation of "16" and "17"

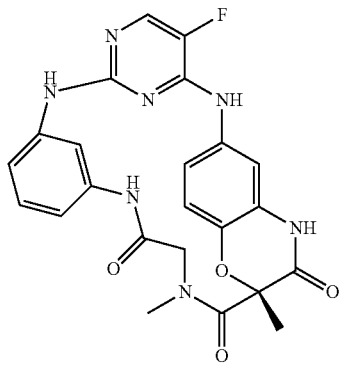
"16"

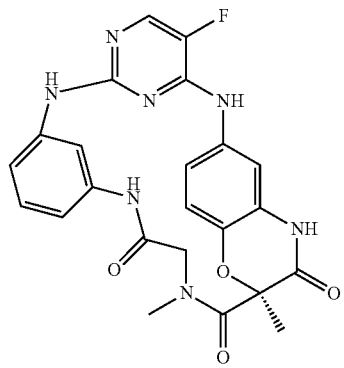
"17"

The racemate 15 (43 mg) is dissolved in 3 mL methanol+ 0.5% diethyl amine. The enantiomers are separated by SFC chromatography (Minigram SFC, 250 mm×4.6 mm Chiralcel OJ-H column, isocratic eluent: CO2+30% 2-propanol+0.5% diethyl amine, flow: 5 mL/min.). Due to precipitation of the racemate in the injection solvent: the racemate is redissolved in more injection solvent several times. In some runs the autosampler tubing of the SFC is jammed due to compound precipitation. The injection needle and other tubing of the autosampler are cleaned and the injection continued. By use of this method, three fractions are collected. The first fraction is the injection solvent peak (methanol), second fraction 10.6 mg of the first eluting enantiomer 16 and third fraction, 8 mg of the second eluting enantiomer 17. The absolute configuration of either compound is not determined.

The following compounds have been prepared analogously

| compound no. | structure and/or name analytical data | HPLC [min]/ MS [M + 1] |
|---|---|---|
| "B1" | | |
| "B2" | | |

| compound no. | structure and/or name analytical data | HPLC [min]/ MS [M + 1] |
|---|---|---|
| "B3" | 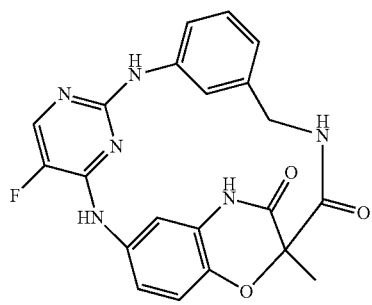 [SMILES: CC12Oc3ccc(cc3NC1=O)Nc1nc(ncc1F)Nc1cccc(c1)CNC2=O] | 0.76/421.6 |
| "B4" | 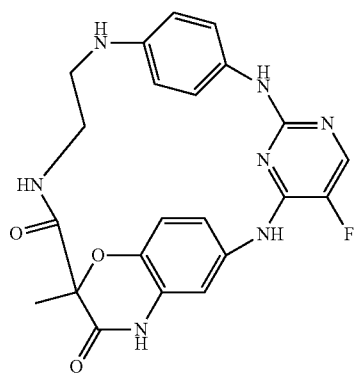 [SMILES: CC12Oc3ccc(cc3NC1=O)Nc1nc(ncc1F)Nc1ccc(cc1)NCCNC2=O] | 0.69/450.5 |
| "B5" | 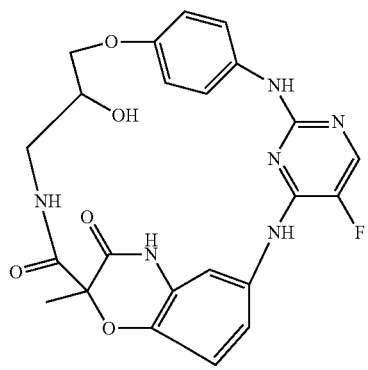 [SMILES: CC12OC3=C(C=C(C=CC3)Nc3nc(ncc3F)Nc3ccc(cc3)OCC(O)CNC1=O)NC2=O] | 0.68/481.9 |
| "B6" | 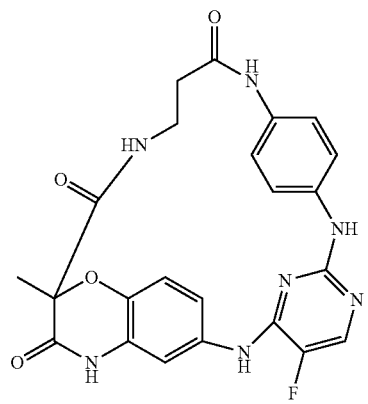 [SMILES: CC12Oc3ccc(cc3NC1=O)Nc1nc(ncc1F)Nc1ccc(cc1)NC(=O)CCNC2=O] | 0.65/478.7 |

| compound no. | structure and/or name analytical data | HPLC [min]/ MS [M + 1] |
|---|---|---|
| "B7" | | 0.71/578.0 |
| "B8" | | 0.71/591.9 |
| "B9" | | 0.68/606.0 |
| "B10" | | 0.77/449.5 |

| compound no. | structure and/or name analytical data | HPLC [min]/ MS [M + 1] |
|---|---|---|
| "B11" | 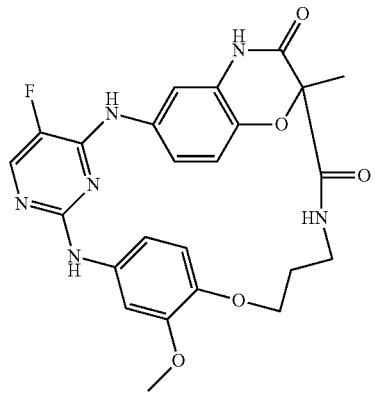 [SMILES: COc1cc2ccc1OCCCNC(=O)C1(C)Oc3ccc(cc3NC1=O)Nc1nc(ncc1F)N2] | 0.74/495.6 |
| "B12" | 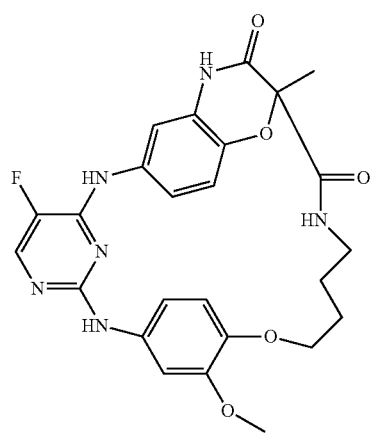 [SMILES: COc1cc2ccc1OCCCCNC(=O)C1(C)Oc3ccc(cc3NC1=O)Nc1nc(ncc1F)N2] | 0.79/509.7 |
| "B13" | 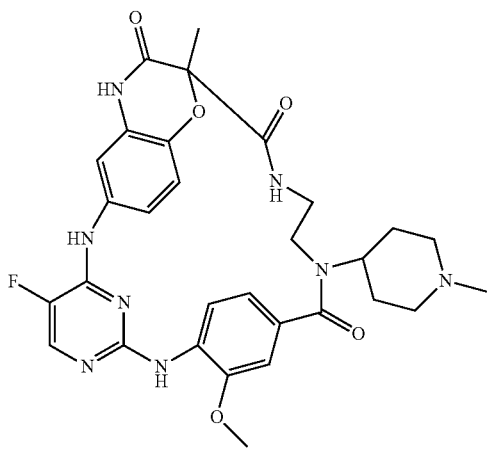 [SMILES: COc1cc2ccc1Nc1ncc(F)c(n1)Nc1ccc3c(c1)NC(=O)C(C)(O3)C(=O)NCCN(C1CCN(C)CC1)C2=O] | 0.64/605.8 |

-continued
| compound no. | structure and/or name analytical data | HPLC [min]/ MS [M + 1] |
|---|---|---|
| "B14" | 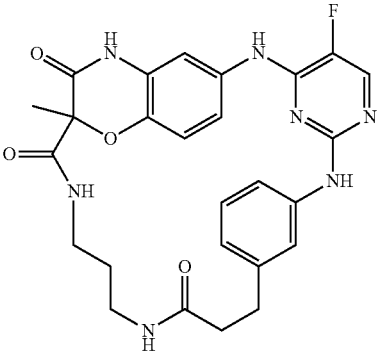 [SMILES: CC12Oc3ccc(cc3NC1=O)Nc1nc(ncc1F)Nc1cccc(c1)CCC(=O)NCCCNC2=O] | 0.96/521.0 |
| "B15" | 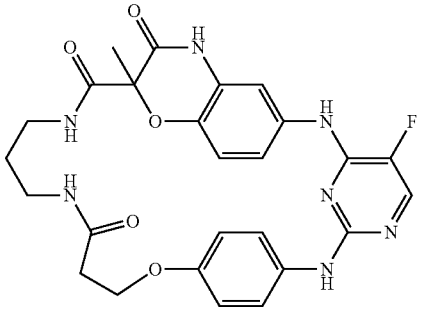 [SMILES: CC12Oc3ccc(cc3NC1=O)Nc1nc(ncc1F)Nc1ccc(cc1)OCCC(=O)NCCCNC2=O] | 1.01/536.9 |
| "B16" | 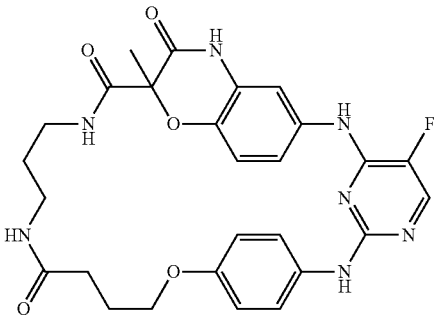 [SMILES: CC12Oc3ccc(cc3NC1=O)Nc1nc(ncc1F)Nc1ccc(cc1)OCCCC(=O)NCCCNC2=O] | 1.05/551.0 |
| "B17" | 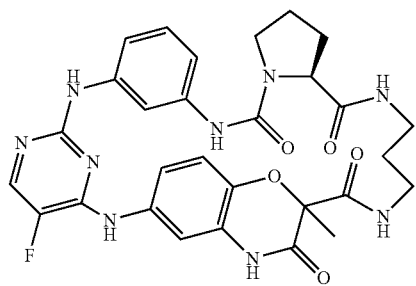 [SMILES: CC12Oc3ccc(cc3NC1=O)Nc1nc(ncc1F)Nc1cccc(c1)NC(=O)N1CCC[C@H]1C(=O)NCCCNC2=O] | 1.00/605.4 |

-continued
| compound no. | structure and/or name analytical data | HPLC [min]/ MS [M + 1] |
|---|---|---|
| "B18" | 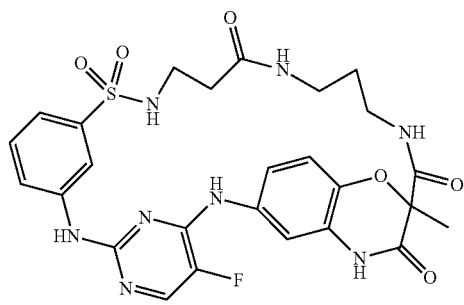 [SMILES: CC12Oc3ccc(cc3NC1=O)Nc1nc(ncc1F)Nc1cccc(c1)S(=O)(=O)NCCC(=O)NCCCNC2=O] | 1.00/600.1 |
| "B19" | 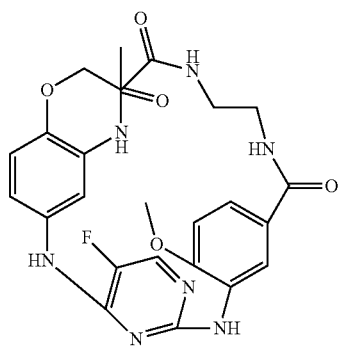 | 0.92/508.7 |
| "B20" | 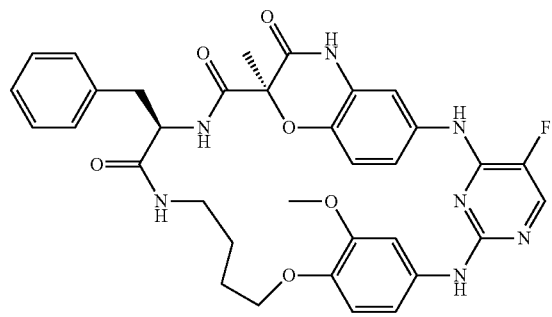 [SMILES: COc1cc2ccc1OCCCCNC(=O)[C@@H](Cc1ccccc1)NC(=O)[C@]1(C)Oc3ccc(cc3NC1=O)Nc1nc(ncc1F)N2] | 1.21/657.6 |
| "B21" | 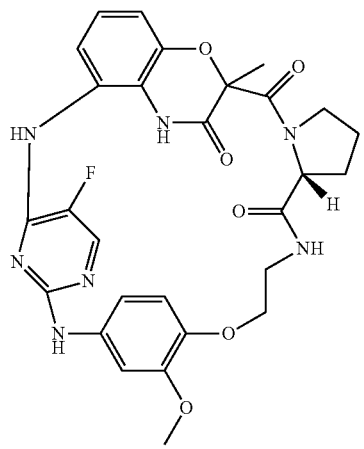 [SMILES: COc1cc2ccc1OCCNC(=O)[C@H]1CCCN1C(=O)C1(C)Oc3cccc(c3NC1=O)Nc1nc(ncc1F)N2] | 1.08/579.0 |

| compound no. | structure and/or name analytical data | HPLC [min]/ MS [M + 1] |
|---|---|---|
| "B22" | 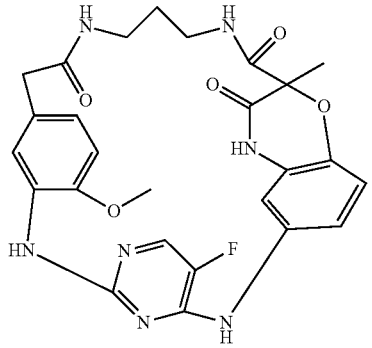 [SMILES: COc1ccc2cc1Nc1ncc(F)c(n1)Nc1ccc3c(c1)NC(=O)C(C)(O3)C(=O)NCCCNC(=O)C2] | 0.98/537.0 |
| "B23" | 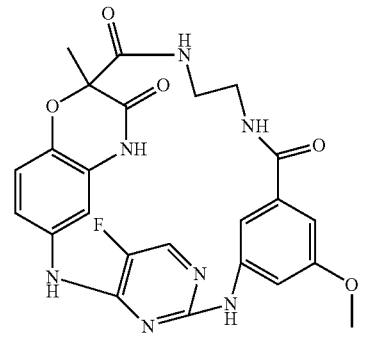 [SMILES: COc1cc2cc(c1)C(=O)NCCNC(=O)C1(C)Oc3ccc(cc3NC1=O)Nc1nc(ncc1F)N2] | 0.93/508.9 |
| "B24" | 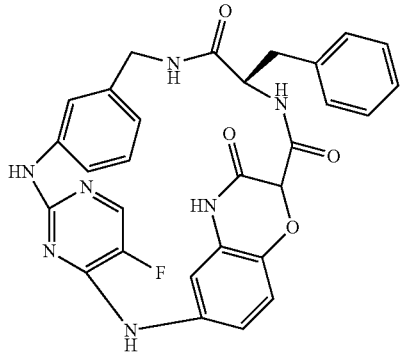 [SMILES: O=C1Nc2cc3ccc2OC1C(=O)N[C@@H](Cc1ccccc1)C(=O)NCc1cccc(c1)Nc1ncc(F)c(n1)N3] | 1.20/569.2 |
| "B25" | 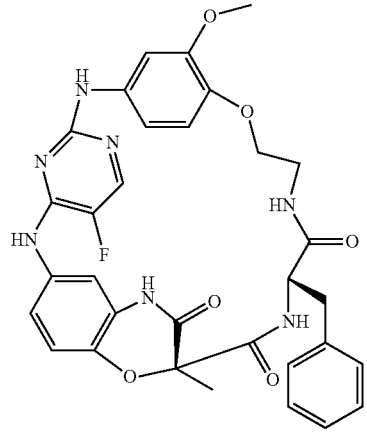 [SMILES: COc1cc2ccc1OCCNC(=O)[C@H](Cc1ccccc1)NC(=O)[C@]1(C)Oc3ccc(cc3NC1=O)Nc1nc(ncc1F)N2] | 1.23/629.2 |

| compound no. | structure and/or name analytical data | HPLC [min]/ MS [M + 1] |
|---|---|---|
| "B26" | | 0.98/605.3 |
| "B27" | | 1.24/657.6 |
| "B28" | | 1.22/629.2 |

Pharmacological Data

TABLE 1

Syk and GCN2 inhibition of some representative compounds of the formula I

| Compound No. | IC$_{50}$ SYK (enzyme assay) | IC$_{50}$ GCN2 (enzyme assay) |
|---|---|---|
| "6" | A | |
| "9" | A | |
| "12" | C | C |
| "15" | A | B |
| "16" | B | C |
| "17" | A | B |
| "B1" | C | |
| "B2" | A | |
| "B3" | −21% * | |
| "B4" | −17% | |
| "B5" | C | |
| "B6" | −5% | |
| "B7" | C | |
| "B8" | −11% | |
| "B9" | −1% | |
| "B10" | −7% | |
| "B11" | C | B |
| "B12" | C | B |
| "B13" | −7% | |
| "B14" | −9% | |
| "B15" | B | |
| "B16" | B | |
| "B17" | C | |
| "B18" | −14% | B |
| "B19" | B | |

TABLE 1-continued

Syk and GCN2 inhibition
of some representative compounds of the formula I

| Compound No. | IC$_{50}$ SYK (enzyme assay) | IC$_{50}$ GCN2 (enzyme assay) |
|---|---|---|
| "B20" | B | C |
| "B21" | | |
| "B22" | −14% | |
| "B23" | B | B |
| "B24" | −23% | |
| "B25" | B | |
| "B26" | | |
| "B27" | −40% | |
| "B28" | −14% | |

IC$_{50}$: < 0.3 µM = A   0.3 – 3 µM = B   3–50 µM = C
* 100% corresponds to zero effect
− 50% corresponds to IC$_{50}$ The compounds shown in Table 1 are particularly preferred compounds according to the invention.

The following examples relate to medicaments:

EXAMPLE A

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient of the formula I, 9.38 g of NaH$_2$PO$_4$.2 H$_2$O, 28.48 g of Na$_2$HPO$_4$.12 H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:

1. A compound of formula I

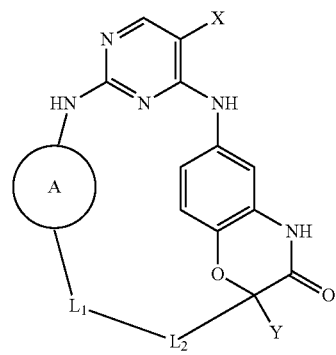

in which:

denotes phenylen or 2,3-dihydro-indo-1,6-diyl, each of which is unsubstituted or monosubstituted by OA, X denotes Hal, Y denotes alkyl having 1, 2, 3 or 4 C atoms, L$_1$ denotes (CH$_2$)$_n$NR$^1$CO, (CH$_2$)$_n$, NH(CH$_2$)$_n$, OCH$_2$CHOH, NHCO(CH$_2$)$_n$, CO(CH$_2$)$_n$NR$^1$, CONR$^2$, (CH$_2$)$_n$, CONR$^1$, O(CH$_2$)$_p$CONR$^1$, NR$^1$CONR$^3$CHR$^4$CONR$^1$, SO$_2$NR$^1$(CH$_2$)$_p$CONR$^1$ or O(CH$_2$)$_p$NR$^1$CO, L$_2$ denotes O(CH$_2$)$_p$, (CH$_2$)$_n$NR$^1$CO, O(CH$_2$)$_p$NR$^1$CO, CHR$^5$NR$^1$CO or CHR$^3$NR$^4$CO, each R$^1$ is independently H or methyl, R² denotes piperidinyl, piperazinyl, pyrrolidinyl, morpholinyl, 2,3-dihydro-pyrazolyl, 1,2-dihydro-pyridyl or tetrahydropyranyl, each of which is unsubstituted or mono- or disubstituted by A and/or =O, R³ and R⁴ together denote independently at each instance an alkylene chain having 2,3 or 4 CH₂ groups, R⁵ denotes A or benzyl, each A is independently an unbranched or branched alkyl having 1-10 C atoms, in which 1-7 H atoms may be replaced by F and/or in which one or two non-adjacent CH and/or CH2 groups may be replaced by O or N, Hal denotes F, Cl, Br or I, each n is independently 0, 1, 2, 3 or 4, each p is independently 1, 2, 3 or 4, or pharmaceutically acceptable salts, tautomers and stereoisomers thereof, including mixtures thereof in all ratios.

2. The compound according to claim 1, selected from the group consisting of:

| No. | Name and/or structure |
|---|---|
| "6" | [structure] |
| "9" | [structure] |
| "12" | [structure] |
| "15" | [structure] |
| "16" | [structure] |
| "17" | [structure] |
| "B1" | [structure] |
| "B2" | [structure] |

| No. | Name and/or structure |
|---|---|
| "B3" | 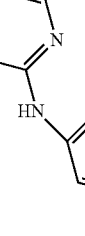 |
| "B4" | |
| "B5" | |
| "B6" | |
| No. | Name and/or structure |
|---|---|
| "B7" |  |
| "B8" | |
| "B9" | |
| "B10" | |

| No. | Name and/or structure |
|---|---|
| "B11" | 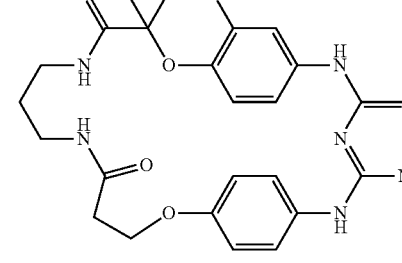 |
| "B12" | |
| "B13" | |
| "B14" | |
| No. | Name and/or structure |
|---|---|
| "B15" | 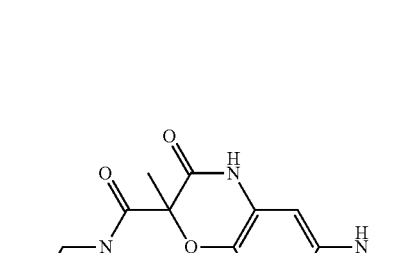 |
| "B16" | |
| "B17" | |
| "B18" | |

| No. | Name and/or structure |
|---|---|
| "B19" | 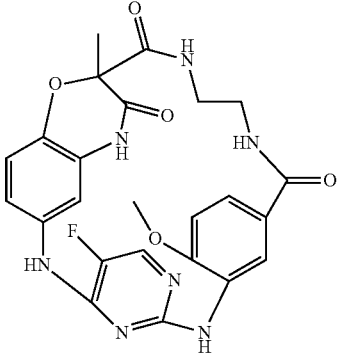 [SMILES: COc1ccc2cc1Nc1ncc(F)c(n1)Nc1ccc3c(c1)NC(=O)C(C)(O3)C(=O)NCCNC2=O] |
| "B20" | 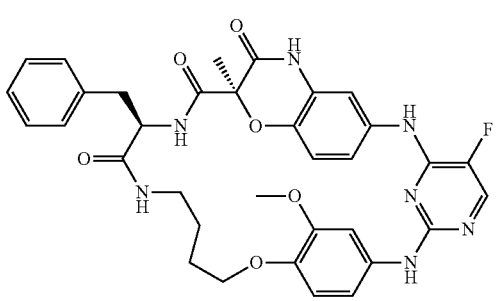 [SMILES: COc1cc2ccc1OCCCCNC(=O)[C@@H](Cc1ccccc1)NC(=O)[C@]1(C)Oc3ccc(cc3NC1=O)Nc1nc(ncc1F)N2] |
| "B21" | 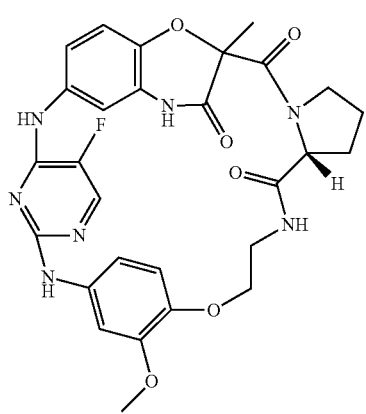 [SMILES: COc1cc2ccc1OCCNC(=O)[C@H]1CCCN1C(=O)C1(C)Oc3ccc(cc3NC1=O)Nc1nc(ncc1F)N2] |
| "B22" | 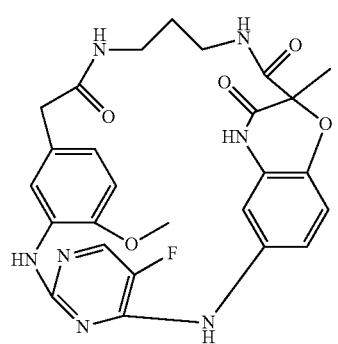 [SMILES: COc1ccc2cc1Nc1ncc(F)c(n1)Nc1ccc3c(c1)NC(=O)C(C)(O3)C(=O)NCCCNC(=O)C2] |
| "B23" | 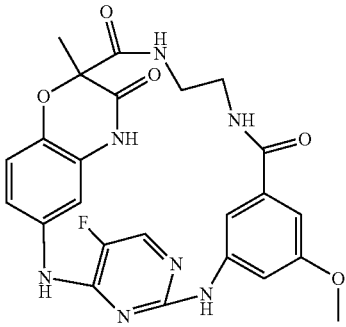 [SMILES: COc1cc2cc(c1)C(=O)NCCNC(=O)C1(C)Oc3ccc(cc3NC1=O)Nc1nc(ncc1F)N2] |
| "B24" | 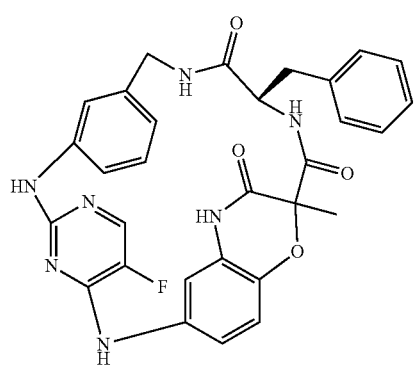 [SMILES: CC12Oc3ccc(cc3NC1=O)Nc1nc(ncc1F)Nc1cccc(c1)CNC(=O)[C@H](Cc1ccccc1)NC2=O] |
| "B25" | 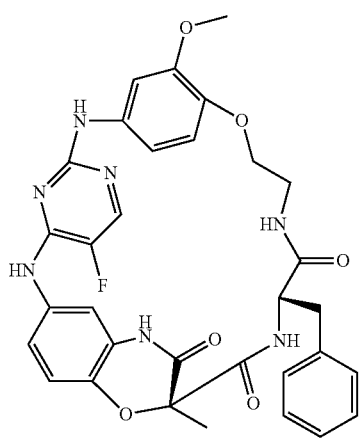 [SMILES: COc1cc2ccc1OCCNC(=O)[C@H](Cc1ccccc1)NC(=O)[C@]1(C)Oc3ccc(cc3NC1=O)Nc1nc(ncc1F)N2] |
| "B26" | 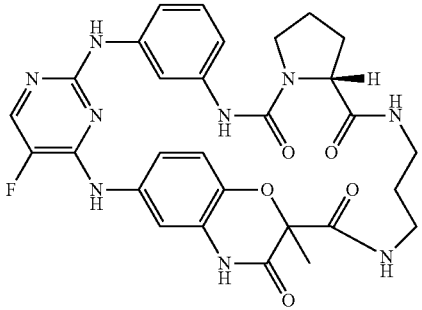 [SMILES: CC12Oc3ccc(cc3NC1=O)Nc1nc(ncc1F)Nc1cccc(c1)NC(=O)N1CCC[C@@H]1C(=O)NCCCNC2=O] |

| No. | Name and/or structure |
|---|---|
| "B27" | 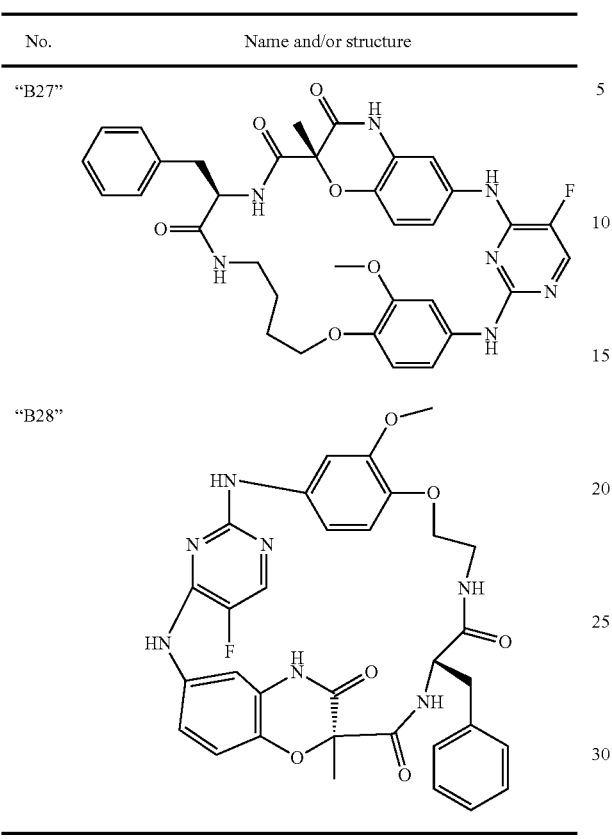 |
| "B28" | | or pharmaceutically acceptable salts, tautomers and stereoisomers thereof, including mixtures thereof in all ratios.

3. A process for the preparation of compounds of formula I according to claim 1 or pharmaceutically acceptable salts, tautomers and stereoisomers thereof, characterised in that a compound of the formula II $L_1$, $L_2$, X and Y have the meanings indicated in claim 1, is cyclized, or a base or acid of the formula I is converted into one of its salts.

4. A pharmaceutical composition comprising at least one compound of formula I or pharmaceutically acceptable salts, tautomers and stereoisomers thereof, including mixtures thereof in all ratios, and optionally an pharmaceutically acceptable carrier, excipient or vehicle.

5. The composition of claim 4 further comprising at least one further medicament active ingredient.

6. A kit consisting of separate packs of:
(a) an effective amount of a compound of formula I of claim 1 or pharmaceutically acceptable salts, salts and stereoisomers thereof, including mixtures thereof in all ratios,
and
(b) an effective amount of a further medicament active ingredient.

* * * * *